United States Patent [19]

Fu et al.

[11] Patent Number: 4,803,625
[45] Date of Patent: Feb. 7, 1989

[54] PERSONAL HEALTH MONITOR

[75] Inventors: Ping W. Fu, Des Plaines; Thomas J. Manning, Chicago, both of Ill.

[73] Assignee: Buddy Systems, Inc., Northbrook, Ill.

[21] Appl. No.: 879,900

[22] Filed: Jun. 30, 1986

[51] Int. Cl.$^4$ .............................................. G06F 15/42
[52] U.S. Cl. .......................... 364/413.03; 364/413.02; 128/906; 128/908
[58] Field of Search ........... 364/415, 479, 416, 413.02, 364/413.03, 200 MS File, 900 MS File; 128/908, 906, 900, 904

[56] References Cited

U.S. PATENT DOCUMENTS

| | | | |
|---|---|---|---|
| 3,426,150 | 2/1969 | Tygart | 179/2 |
| 3,910,257 | 10/1975 | Fletcher | 128/908 |
| 3,996,928 | 12/1976 | Marx | 364/415 X |
| 4,004,577 | 1/1977 | Sarnoff | 128/2.06 R |
| 4,130,881 | 12/1978 | Haessler | 364/415 X |
| 4,150,284 | 4/1979 | Trenkler et al. | 250/199 |
| 4,151,831 | 5/1979 | Lester | 364/415 X |
| 4,173,971 | 11/1979 | Karz | 128/702 |
| 4,216,462 | 8/1980 | McGrath | 364/415 X |
| 4,227,526 | 10/1980 | Goss | 128/214 E |
| 4,270,547 | 6/1981 | Steffen | 128/671 |
| 4,296,756 | 10/1981 | Dunning et al. | 128/716 |
| 4,417,306 | 11/1983 | Citron et al. | 364/415 |
| 4,422,081 | 12/1983 | Woods | 346/33 ME |
| 4,465,077 | 8/1984 | Schneider | 128/738 |
| 4,473,884 | 9/1984 | Behl | 364/479 |
| 4,513,294 | 4/1985 | Anderson et al. | 346/33 ME |
| 4,519,398 | 5/1985 | Lisiecki | 128/710 |
| 4,531,527 | 7/1985 | Reinhold et al. | 128/696 |
| 4,674,652 | 6/1987 | Aten | 364/479 X |
| 4,695,954 | 9/1987 | Rose et al. | 364/415 |
| 4,712,562 | 12/1987 | Ohayon et al. | 128/672 |
| 4,731,726 | 3/1988 | Allen | 422/55 X |

Primary Examiner—Jerry Smith
Assistant Examiner—Steven G. Kibby
Attorney, Agent, or Firm—Willian, Brinks, Olds, Hofer, Gilson & Lione Ltd.

[57] ABSTRACT

A personal health monitor includes sensors for measuring patient weight, temperature, blood pressure, and ECG waveform. The monitor is coupled to a central unit via modems and includes a computer which is programmed to prompt a patient to take prescribed medication at prescribed times, to use the sensors to measure prescribed health parameters, and to supply answers to selected questions. Medication compliance information, test results, and patient answers are compiled in a composite log which is automatically transmitted to the central unit. The computer is also programmed automatically to disconnect the monitor from an alternating current power source and to rely on internal battery power during certain periods of patient-monitor interaction, such as during use of the ECG module. In this way, danger to the patient and complexity of the ECG module are minimized. The computer is also programmed to compare measured test information with predetermined expected values, and in the event of a discrepancy, to collect additional information from the patient to assist trained personnel at the central unit in interpreting the composite log. The computer is also programmed to alert the central unit promptly in the event one or more measured parameters falls outside of a prescribed normal range. The normal range for a given parameter is made to vary in accordance with the measured value of one or more other parameters in order to reduce the incidence of false alarms.

30 Claims, 16 Drawing Sheets

BLOCK DIAGRAM OF NORMAL OPERATION

PERSONAL HEALTH MONITOR

BACKGROUND OF THE INVENTION

This invention relates to improvements to a personal health monitor of the type that automatically collects information indicative of the physical condition of a patient in a log and then transmits the log to a central station for analysis by trained medical personnel.

In the past a wide variety of monitors have been proposed for recording information indicative of the physical condition of a patient. For example, Sarnoff U.S. Pat. No. 4,004,577, Karz U.S. Pat. No. 4,173,971, Citron U.S. Pat. No. 4,417,306, and Lisiecki U.S. Pat. No. 4,519,398 all disclose devices which store information indicative of heart function for later analysis. The Lisiecki device allows the user to record event marker signals to designate particular events on the stored record. Steffen U.S. Pat. No. 4,270,547 discloses a system which monitors multiple parameters, including breathing rate and body temperature, as well as pulse rate and blood pressure.

Dunning U.S. Pat. No. 4,296,756 discloses a remote pulmonary function tester which receives patient identification data, directs a test sequence, and then stores the test results for later transmission to a central computer. The patient identification data are entered in response to questions presented by the tester on a display.

Schneider U.S. Pat. No. 4,465,077 discloses a fertility computer which predicts fertility status based on temperature measurements and user supplied responses to questions related to relevant physiological conditions.

The foregoing patents have been referenced only by way of general background, because none of them relates to the improvements of this invention. As described in detail below, these improvements enhance the diagnostic value of the transmitted log, minimize false alarms to the central station, minimize unnecessary tests on the patient, and minimize the complexity and expense of the monitor itself.

SUMMARY OF THE INVENTION

According to a first feature of this invention, a personal health monitor is provided which comprises means for determining a plurality of health parameters, each indicative of the physical condition of the patient. Means are also provided for prompting the patient with selected messages and for storing a prescribed parameter schedule for selected ones of the health parameters and a prescribed medication schedule for at least one medication. First means automatically control the prompting means to request the patient to use the determining means to determine the selected ones of the health parameters in accordance with the prescribed parameter schedule. This first means stores the determined health parameters in a composite log. Second means automatically control the prompting means to request the patient to take medication in accordance with the prescribed medication schedule, and automatically record information in the composite log indicative of patient compliance with the prescribed medication schedule. The composite log is then automatically transmitted to a central location for analysis by trained medical personnel.

This aspect of the invention provides the advantage that a single monitoring system (1) prompts the patient to take medication in accordance with the prescribed schedule, (2) records patient compliance with the prescribed medication schedule, and (3) records patient health parameters in accordance with the prescribed parameter schedule. Information that will allow trained personnel to determine both patient compliance with the medication schedule and the physical condition of the patient is transmitted in the composite log to the central location. By providing both information regarding physical condition of the patient and patient compliance with the medication schedule, this monitor materially assists medical personnel in assessing the health of the patient. As used herein, the term "health parameters" is intended in its broad sense to encompass both measurements of vital signs such as pulse, blood pressure, ECG and the like, as well as determination of patient symptoms by patient responses to questions.

According to a second feature of this invention, a personal health monitor adapted to be powered by an alternating current power source comprises means for collecting information indicative of the physical condition of the patient, means for recording the collected information, and means for supplying a supply voltage to power the collecting means and the recording means. This supply means comprises a rechargeable battery connected to the collecting means and the recording means, and a battery charger adapted for connection to the alternating current power source and comprising means for supplying a charging current to the battery. The switch is positioned to interrupt the flow of charging current from the battery charger to the battery and is switchable between a first state, in which the switch isolates the battery from the charging current, and a second state, in which the switch allows the charging current to flow to the battery. Means are provided for controlling the switch such that the switch is automatically placed in the first state during selected periods of interaction between the patient and the collecting means, and the switch is automatically placed in the second state during selected periods characterized by an absence of interaction between the patient and the collecting means. Preferably, the switch comprises a latching relay which is interposed between the battery charger and the alternating current power source.

As explained in greater detail below, this feature of the invention provides important advantages in that the battery is not charged during at least selected periods of interaction between the patient and the monitor. Various sensors such as electrocardiogram (ECG) sensors are simplified in that AC ripple associated with the alternating current power source is no longer a potential problem. The cost and complexity of certain sensors such as ECG sensors and related circuitry can therefore be reduced. Furthermore, because the battery is isolated from the AC power source during periods of patient interaction, the AC power source poses no danger to the patient. The need for isolated power supplies and the like to protect the patient from the AC power source is therefore minimized.

According to a third feature of this invention, a personal health monitor is provided which comprises first means for automatically collecting a first set of data indicative of the physical condition of a patient, and second means for automatically comparing the first set of data with a set of test criteria and for indicating when the first set of data fails to meet the test criteria. Third means are provided for automatically collecting a second set of additional data from the patient when the first set of data fails to meet the test criteria. The second set of additional data is selected to provide additional diagnostic information useful in interpreting the first set of data. Means are provided for automatically transmitting the first and second sets of data to a central location for analysis by trained medical personnel. As used herein, the term "set of data" is used in its broad sense to encompass one or more measurements or patient responses.

This aspect of the invention provides a personal health monitor which minimizes inconvenience to the patient while providing attending medical personnel with more complete diagnostic information. As explained in greater detail below, this aspect of the invention allows tests or questions which are not routinely required to be eliminated from the first set of data, thereby minimizing the inconvenience to the patient. Nevertheless, when the first set of data indicates a potential problem, the monitor automatically collects the second set of data in order to provide the medical personnel at the central location with more complete diagnostic information. In this way, the medical personnel at the central location are better able to diagnose the physical condition of the patient. Of course, the first set of data can include data collected over an extended time period and indicative of a trend or data collected in a single measurement or question and answer session.

According to a fourth feature of this invention, a personal health monitor is provided which comprises means for automatically monitoring a plurality of patient parameters indicative of the physical condition of the patient. This plurality of parameters includes at least first and second parameters. In addition, means are provided for storing information indicative of a selected range of normal values of the first parameter. This selected range of normal values varies in accordance with the second parameter, such that the selected range of normal values when the second parameter has a first value is different from the selected range of normal values when the second parameter has a second value. The monitor automatically alerts a central station only when the first parameter is outside the selected range of normal values. As used herein, "normal" is intended broadly to encompass the range of values designated by the physician as normal for a particular patient.

This fourth aspect of the invention provides important advantages in that it reduces the number of false alarms at the central station. As described in detail below, the range of normal values of any one parameter, such as patient temperature or blood pressure, will often vary in accordance with one or more other parameters. By adjusting the selected range of normal values as appropriate for the currently prevailing conditions as indicated by the second parameter, the health monitor is better able to distinguish between situations in which the central station should be alerted of a potential problem, and situations which can be reported in the conventional manner. By reducing false alarms, this aspect of the invention reduces the work load at the central station and thereby improves the efficiency of operation of the system as a whole.

The various features of this invention can be grouped together as desired. For example, the preferred embodiment described below combines all four features together in a single personal health monitor. However, each of these features can be employed independently of the others, if desired.

BRIEF DESCRIPTION OF THE DRAWINGS

FIGS. 15a and 16b are a flowchart of the Exception Handler referenced in routines such as those of FIGS. 4, 5, 6, 11, 12, 13, and 15, for example.

DETAILED DESCRIPTION OF THE PRESENTLY PREFERRED EMBODIMENTS

Figure 1:
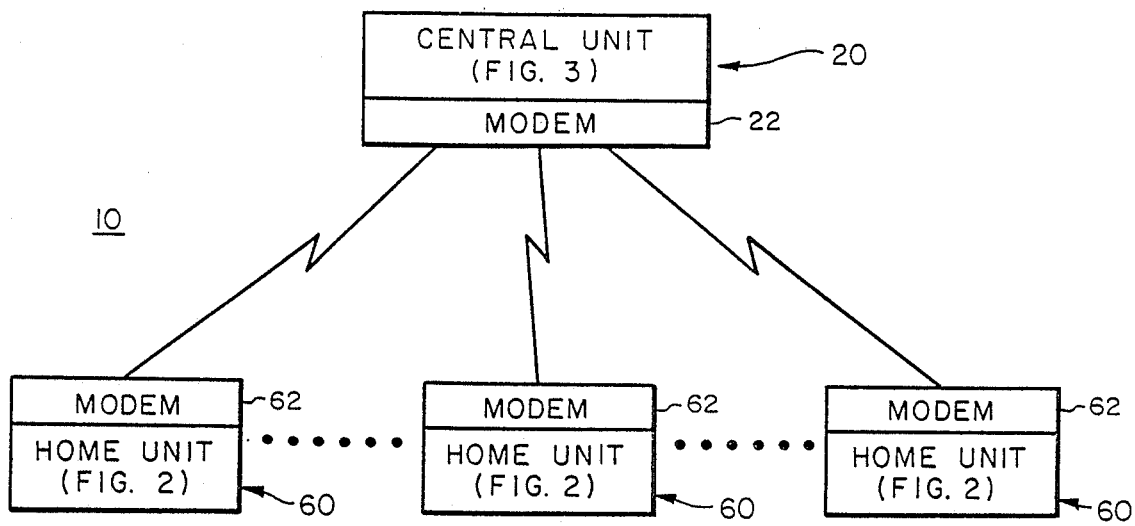
FIG. 1 is a block diagram of a personal health monitoring system which incorporates a presently preferred embodiment of the monitor of this invention.

The following detailed description will take up first the hardware and then the software of the presently preferred embodiment of the personal health monitor of this invention. In general terms, this monitor is designed (1) to prompt the patient to perform tests and to respond to questions as prescribed by a physician having responsibility for the care of the patient; (2) to prompt the patient to take medication as prescribed and to log compliance by the patient; and (3) to communicate the results of the tests, the patient's answers to the questions, and medication compliance information to a central unit staffed with trained medical personnel. The system is made up of two subunits, a home unit adapted for use by a patient in an unsupervised manner in a home setting, and a central unit.

From the point of view of the patient, the personal health monitoring system described below provides important advantages in terms of simplified data entry (for both test results and question responses), automated communication with the central unit, and fast feedback from medical personnel. From the point of view of the physician, this system provides important advantages in terms of better tracking of the vital signs of the patient, better information regarding patient compliance with medication schedules, and a complete log of timestamped vital signs which will help to detect abnormal trends and to prevent catastrophical readmission. For example, a hospital can use the personal health monitoring system described below for follow-up care of those patients who do not need intensive, hospital-based care, yet require some form of personal health monitoring.

In general terms, the home unit operates to log data indicative of various health parameters of the patient on a schedule prescribed by the attending physician. These health parameters include various vital signs such as ECG, body temperature, body weight, blood pressure, heart rate, blood glucose level, and pulmonary functions, along with patient responses to selected questions. The home unit will also log patient volunteered information and the results of patient volunteered tests. The home unit also functions to remind the patient when medication is to be taken and to log patient compliance, including information relating to the time, dosage and type of medication. The home unit is easy for a patient to use and automatically communicates logged information with the central unit based on pre-programmed reporting times plus special reports made in response to triggering events. Preferably, communication is via a modem and appropriate programs are provided to provide retry on error during transmission and redial on error such that no patient intervention is required.

Preferably, the various sensors included in the home unit such as the temperature probe, the ECG electrode probe, the weight scale, the blood pressure device, the ECG signal processing circuitry are designed as modules to minimize obsolescence and to allow new or improved components to be added simply.

The home and central units are constructed from conventional components chosen such that no special room modifications such as air conditioning, special power supplies, or the like are required. The central unit generates reports of logged patient parameters for analysis and response by trained medical personnel. Preferably, software for the central unit is written such that the system can readily be used by a non-computer specialist.

SYSTEM HARDWARE

As shown in FIG. 1, the personal health monitoring system 10 of this preferred embodiment comprises a central unit 20 and a plurality of home or remote units 60. The central unit 20 is linked with each of the home units 60 by respective modems 22, 62. Typically, the central unit 20 is situated at a health care facility, such as a hospital, or at a central health information monitoring facility and each of the home units 60 is situated in the room or home of a respective patient.

Figure 2:
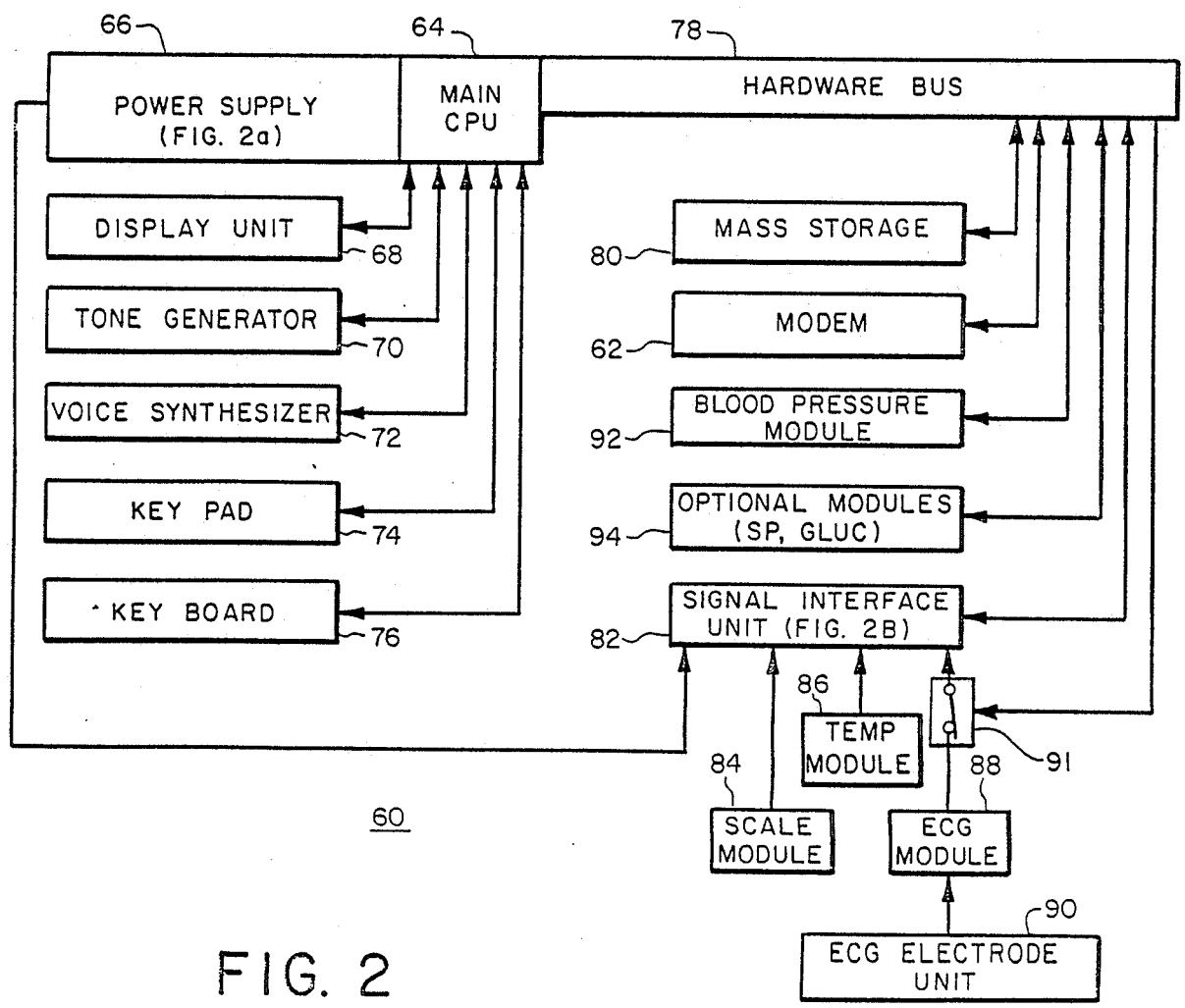
FIG. 2 ia a block diagram of one of the home units of FIG. 1.

FIG. 2 shows a block diagram of one of the home units 60. As shown in FIG. 2, each home unit 60 includes a main CPU 64 which is powered by a power supply 66. The main CPU 64 communicates with the patient via a display unit 68, a tone generator 70, a voice synthesizer 72, and a key pad 74. Preferably, a detachable and portable keyboard 76 is provided which can be used by a health care professional for more detailed interrogation or programming of the home unit 60. Of course, other I/O devices can be included as well, such as touch screens, microphones, and the like. The main CPU 64 is connected via a hardware bus 78 with the modem 62 and a mass storage device 80 for storing digital information. The hardware bus 78 also interconnects the main CPU 64 with a signal interface unit 82 that is in turn connected to a weight scale module 84, a patient temperature module 86, and an electrocardiogram (ECG) module 88. The ECG module 88 is in turn connected to an ECG electrode unit adapted for application to the chest of the patient. A blood pressure module 92 is connected to the main CPU 64 via the bus 78, along with other optional modules 94, such as modules for measuring pulmonary functions or blood glucose level, for example. A relay 91 controlled by the CPU 64 is interposed between the signal interface unit 82 and the ECG module 88 to allow the CPU 64 to ensure that the ECG electrode unit 90 is isolated from any power source.

Figure 2A:
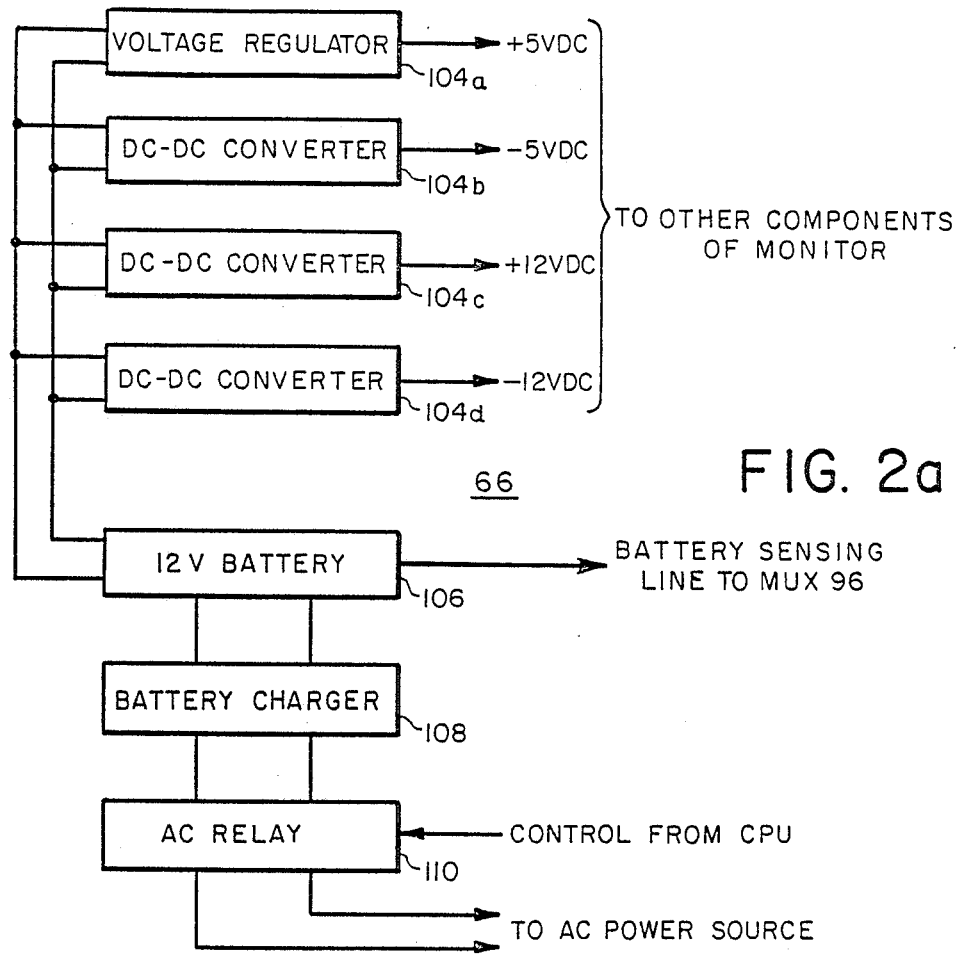
FIG. 2a is a block diagram of the power supply of FIG. 2.
Figure 2B:
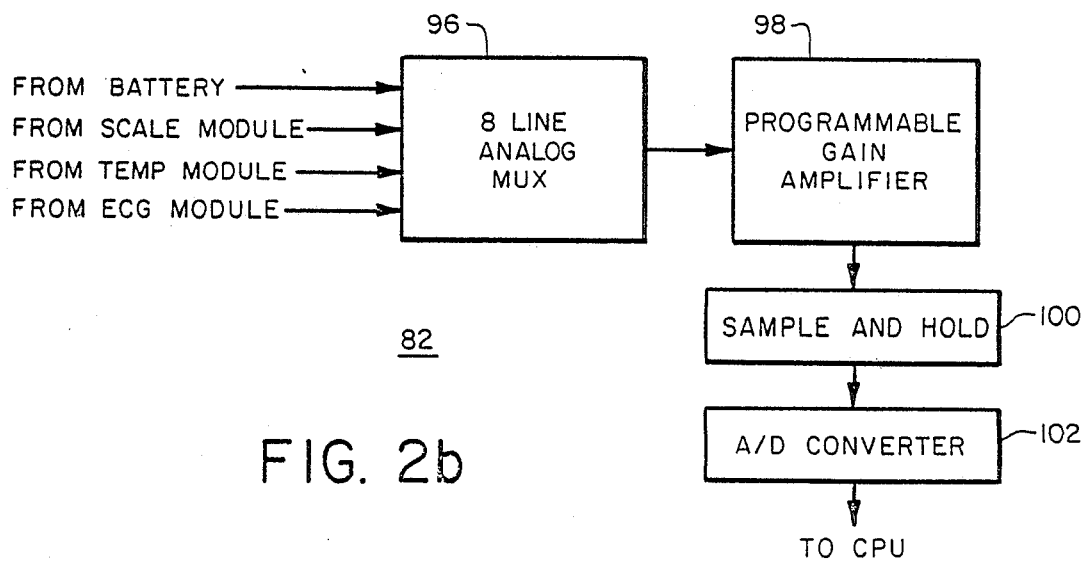
FIG. 2b is a block diagram of the signal interface unit of FIG. 2.

As shown in FIG. 2b, the interface unit 82 includes an eight differential line analog multiplexer 96 which includes inputs connected to receive analog signals from the scale module 84, the temperature module 86, the ECG module 88 and a battery included in the power supply 66. Other inputs to the multiplexer 96 can be used for other sensor inputs, such as additional ECG signals and ambient temperature, for example. The eight differential line analog multiplexer 96 is controlled by the main CPU 64 to select one of the eight input signals, which is passed to a programmable gain instrumentation amplifier 98. After suitable amplification, the selected analog signal is applied as an input to a sample and hold circuit 100 which samples the analog value of the selected amplified signal and holds this sampled value for conversion by an analog to digital converter 102. The resulting digital signal is then read by the main CPU 64 via the hardware bus 78.

Each of the blocks of FIG. 2, with the exception of the power supply 66, is a conventional, readily available hardware component. Without intending in any way to limit the scope of this invention, the following information is provided in order better to define the presently preferred embodiment of the home unit 60.

In the home unit 60 of this embodiment, the main CPU 64 is an IBM PC compatible CPU board, such as the CPU boards available from Faraday, Mostron, IBIS, OEM Tech, or G&L, Inc. The modem 62 is preferably of the type which will transmit both data and voice having an auto dial feature and selectable 300/1200 baud data rates, such that the modem can be plugged directly into a regular phone line. Suitable modems are available from U.S. Robotics, Hayes, Qubie, and Racal-Vadic. The display unit 68 is preferably a nine inch CRT monitor, having a minimum bandwidth of 15 MHz. Suitable monitors are available from Hitachi, Tatung, GoldStar and SamSung, for example. The voice synthesizer 70 is preferably based on the Texas Instruments Digitalker chip set available from Texas Instruments. The portable keyboard 76 is preferably a hand-held unit with limited display capability using liquid crystal display with back lighting. A suitable device is available from Radio Shack as the TRS 80- Model 100. The bus 78 is preferably based on the IBM PC I/O slot with 62 connections. The mass storage device 80 is preferably a 3.5 inch mini-floppy disc drive having at least 500K bytes of formatted storage space. Suitable drives are available from Sony (MP-F53W-00D), Fujitsu (M2532A), and Panasonic (Ju-346-14). The signal interface unit 82 preferably incorporates a 12-bit A-D converter 102. MetraByte markets a suitable signal interface unit 82 as Model No. DASH-8.

In this embodiment, each of the sensor modules is a conventional component. For example, the scale module 84 is preferably an electronic solid-state weight scale having a range from 15 pounds to 300 pounds with 0.5 pound accuracy, such as the device sold by Norelco. The temperature module preferably has a temperature range of 65°-110° F. with a 0.2° F. accuracy. Suitable temperature modules are available from Labtron and Yellow Spring Instrument. The ECG module 88 preferably includes low-pass filtering, appropriate gain, transient suppression, common mode rejection, and signal isolation for two-lead ECG signals. A suitable device is available from Scole Engineering. The ECG electrode unit 90 is preferably of the type using pre-gelled electrodes or bandage-type electrodes. Suitable devices are available from NDM, Cardio-Dynamics Sentry Medical, and TDK. The blood pressure module 92 is an automatic blood pressure monitor with digital I/O capability, such as the devices marketed by Takeda Medical and Norelco.

Turning now to FIG. 2a, the power supply 66 includes a +5V DC regulator 104a and three DC-DC converters 104b, 104c, 104d which provide DC voltages to the remaining components of the home unit 60 at +5 VDC, −5 VDC, +12 VDC, and −12 VDC, respectively. These regulators and DC-DC converters 104a-104d are powered by a rechargeable battery 106 which in this embodiment is preferably a sealed 12 volt lead-acid rechargeable battery. The rechargeable battery 106 is charged by a battery charger 108 which is connected via an AC latching relay 110 to an alternating current source such as a home wall outlet which provides alternating current at 120 volts AC. A suitable battery charger and battery can be obtained from Sonnenschein. One of the input signals to the multiplexer 96 is connected to the battery 106 to allow the main CPU 64 to measure the voltage developed by the battery 106 in order to assess the condition of the battery. The relay 110 is controlled by the main CPU 64 such that the main CPU 64 can interconnect the battery charger 108 with the alternating current power source, or alternately isolate the battery charger 108 from the alternating power source. As explained in detail below, the main CPU 64 isolates the battery charger 108 and the battery 106 from the source of alternating current when the patient interacts with the home unit 60. In this way, the complexity and cost of components such as the ECG module 88 are reduced because AC ripple voltages associated with the AC power source are eliminated. Furthermore, the patient is protected completely from unintended contact with the AC power source, even in the absence of isolated power supplies.

Figure 3:
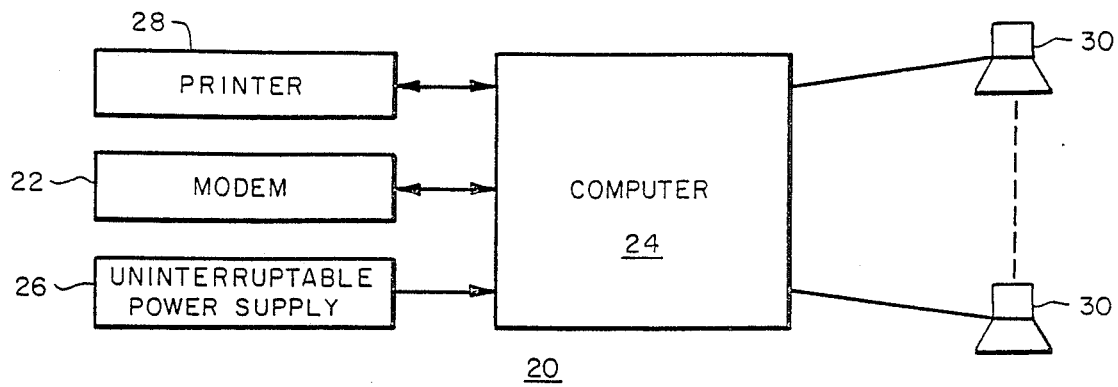
FIG. 3 is block diagram of the central unit of FIG. 1.

FIG. 3 shows a block diagram of the central unit 20. The central unit 20 includes a super microcomputer 24 which is supplied with regular AC power backed up by an uninterruptible power supply 26. The central unit 20 controls a printer 28, and a number of operators which may include trained medical personnel interact with the computer 24 via respective terminals 30.

Simply by way of example, the computer 24 may be a 16/32 bit microcomputer with one MB of RAM, one high density floppy disk drive, and a 20-80 MB mass storage disk drive. Suitable microcomputers are available from AT&T (3B2-400, PC-UNIX), IBM (AT, RT, or System 36), DEC (Micro VAX II), SBE (multibus based). The uninterruptible power supply 26 preferably has a minimum holding power suitable for 20 minutes of operation with a power drain of 600 watts. A suitable system can be obtained from PARA Systems, Inc. The printer 28 can be any suitable printer such as a dot matrix printer with graphic capabilities such as those obtainable from Epson, Panasonics, Okidata or Facit. Any conventional CRT terminal can be used for the terminal 30, such as those available from Kimtron, Televideo, Wyse, or Ampex.

The microcomputer 24 is preferably programmed with a multi-user, multi-tasking operating system such as the UNIX system which includes suitable programs for receiving communications from the home units 60, preparing appropriate reports, and directing appropriate instructions or data files to the respective home units 60.

The central unit 20 has been described merely to provide a fuller explanation of the environment of this invention. The details of structure and operation of the central unit 20 form no part of this invention, and therefore will not be described in any greater detail here.

SOFTWARE OF THE HOME UNIT

As described briefly above, the home unit 60 is programmed to prompt the patient to perform prescribed tests and to take prescribed medication, all in accordance with predetermined test and medication schedules. The measurements obtained from the tests and information indicative of patient compliance with the medication schedule are stored in a composite log, which is automatically transmitted to the central unit 20 for analysis by trained personnel. As pointed out in detail below, the software of the home unit 60 controls the power supply 66 to isolate the home unit 60 from the alternating current power source during periods of interaction between the patient and the home unit 60. In addition, the software analyzes parameters indicative of the results of the tests and the answers by the patient to preselected questions and in certain cases supplements the composite log with the results of additional tests or the answers to additional questions in order to facilitate interpretation of the composite log by trained personnel reviewing reports generated by the central unit 20. In addition, this software compares test results with predetermined expected and normal ranges and alerts the central station in the event of a problem. In order to reduce the number of unnecessary alerts, the software uses a sophisticated multiparameter approach which varies the range of acceptable normal values for a first parameter in accordance with the value of at least one additional parameter.

Figure 4:
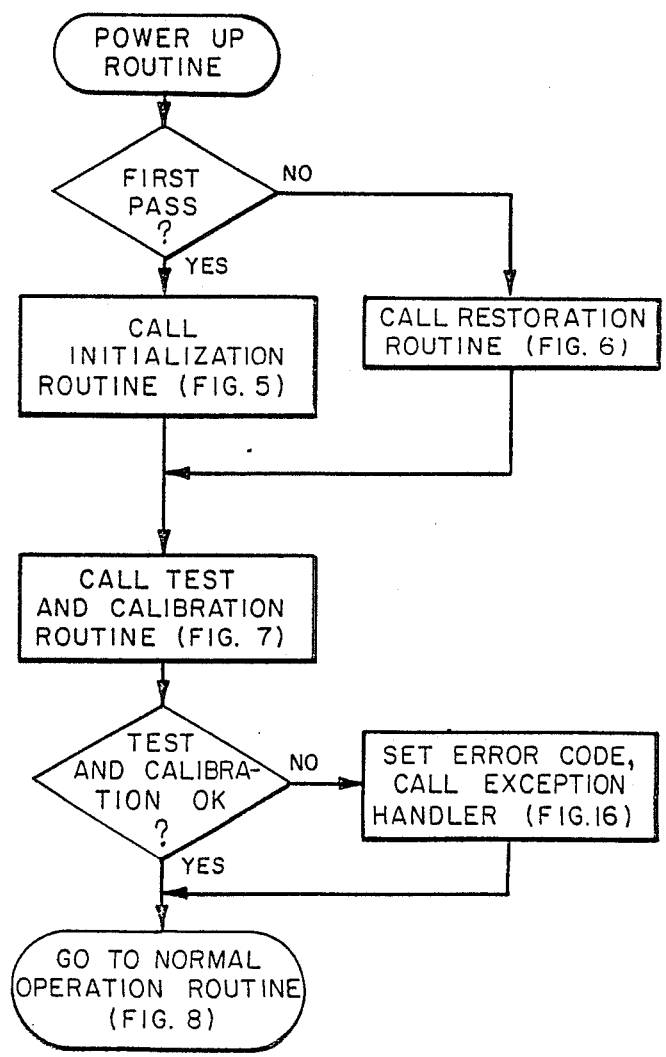
FIG. 4 is a flowchart of the Power-Up Routine of the home unit of FIG. 2.
Figure 5:
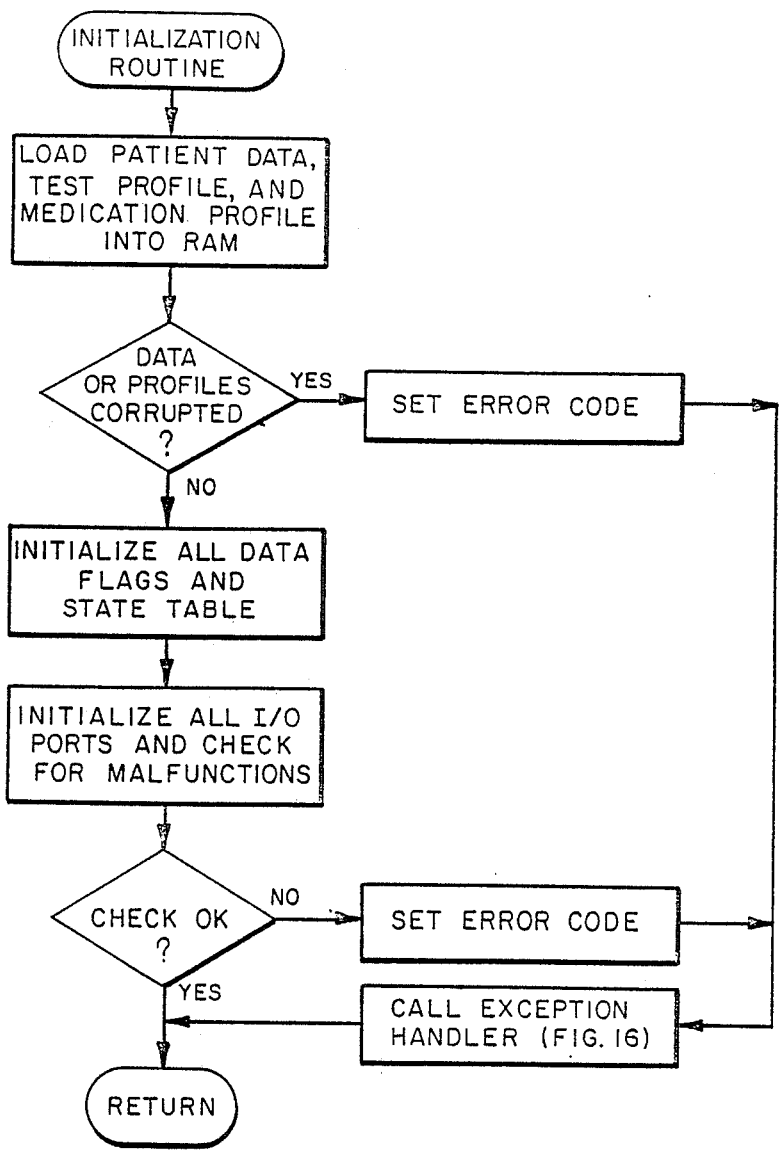
FIG. 5 is a flowchart of the Initialization Routine of FIG. 4.

FIG. 4 shows the general flow of initial processing of the program of the home unit 60 after power is supplied to the home unit 60. During the initial power-up procedure, the entire system is initialized as shown in FIG. 5. Patient data and the test and medication profiles are read from the mass storage device 80 and stored in the random access memory of the main CPU 64. Typically, the patient data will include physician selected information identifying the patient, and providing such information as name, age, sex, address, social security number, telephone number and the like. The test and medication profiles are physician prescribed profiles which define the identity and schedule of tests to be performed and the identity and dosage of medication to be administered. In addition, the test and medication profiles include the physician's designations as to which of the tests and medications are to be deemed critical, along with expected values for each of the parameters measured in the tests and questions to be asked of the patient at selected times.

Simply by way of example, the test profile for a given patient might prescribe that patient weight be measured once a day, and that patient temperature and blood pressure be measured four times a day. By way of example, the medication profile might prescribe that medication A be administered four times a day and that medication B be administered six times a day.

Figure 16A:
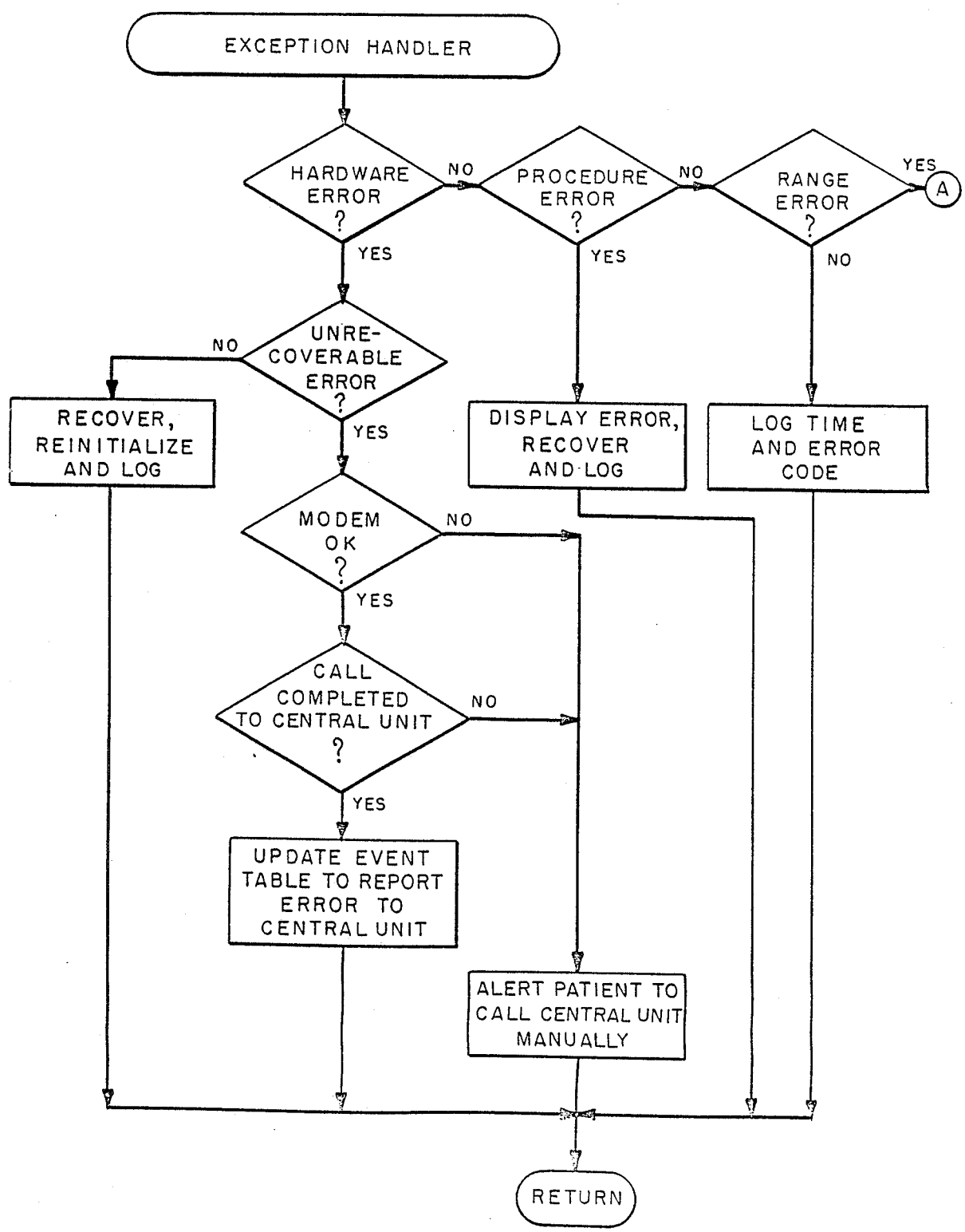
Figure 16B:
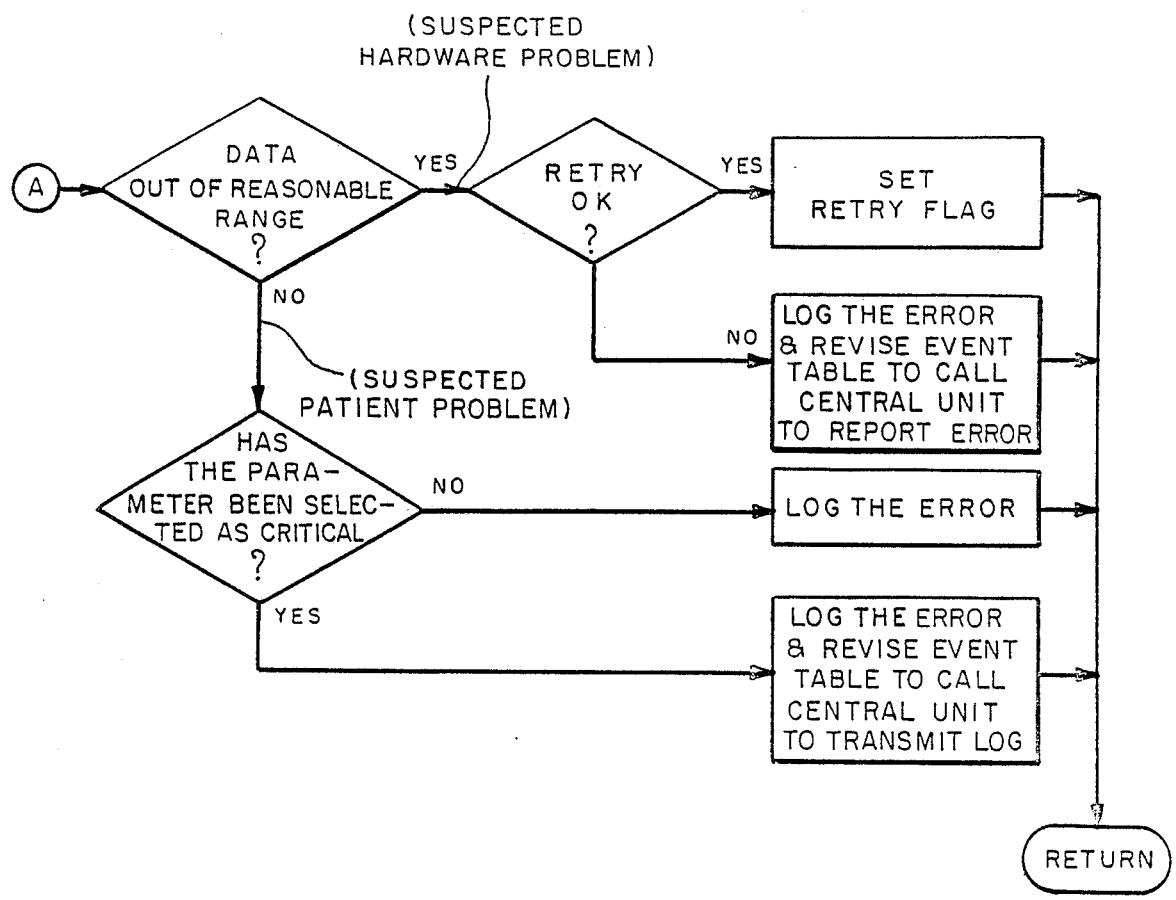

As shown in FIG. 5, after patient data and the test and medication profiles have been loaded into RAM, the integrity of the data and profile files are checked. In the event that these files are found to have been corrupted, an error code is set and the Exception Handler of FIG. 16 is called. Otherwise, various data flags and variables of the state table as described in greater detail below are initialized. Then the various I/O ports of the main CPU 64 are initialized and checked. In the event of a failure, an appropriate error code is set and the Exception Handler of FIG. 16 is called. Otherwise, the Initialization Routine of FIG. 5 returns.

Figure 6:
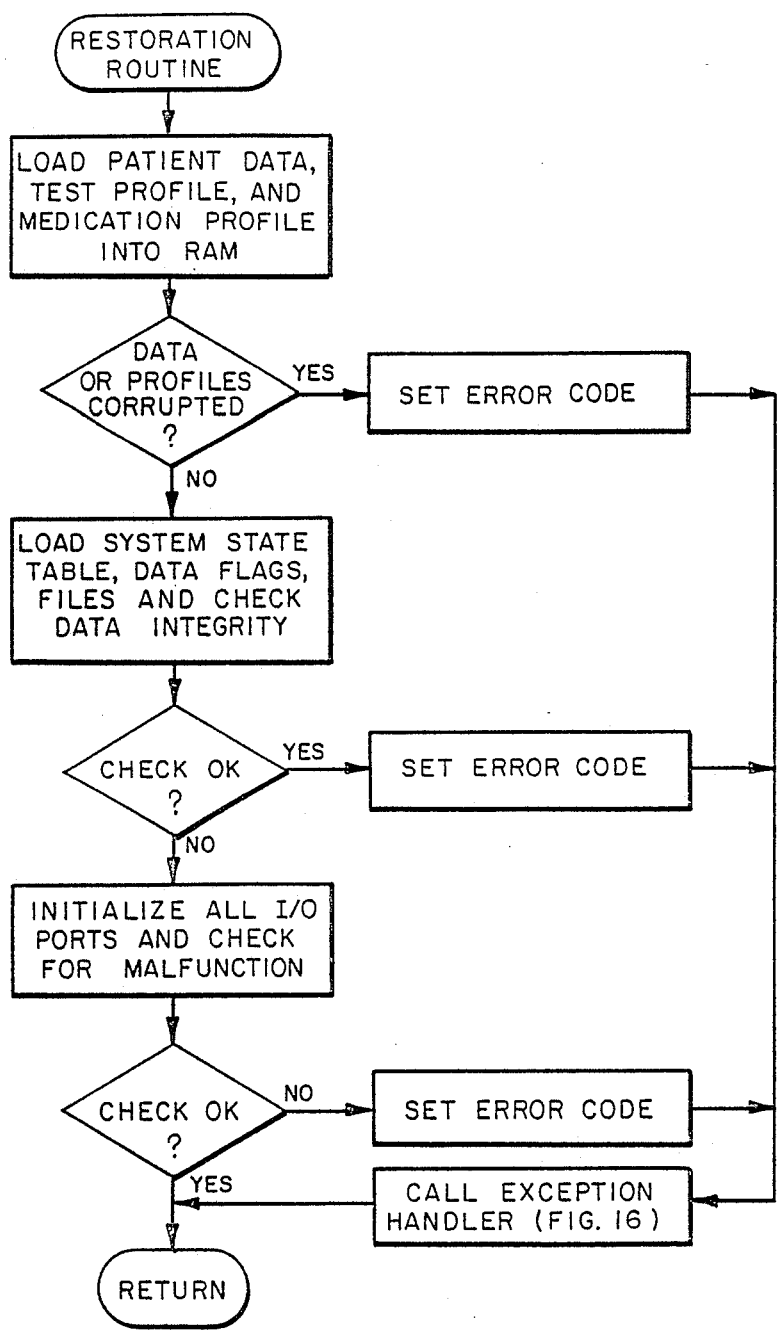
FIG. 6 is a flowchart of the Restoration Routine of FIG. 4.

The Restoration Routine of FIG. 6 is similar to the Initialization Routine of FIG. 5, except that the Restoration Routine is performed in subsequent powerup cycles. Instead of initializing data flags and variables of the state table, the restoration routine loads previously stored data flags and the system state table from the disk into RAM.

Figure 7:
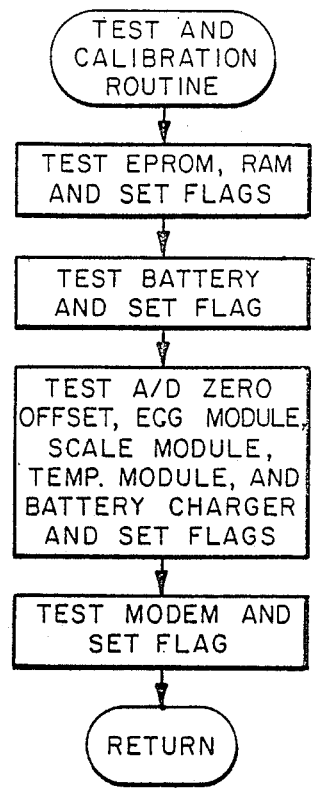
FIG. 7 is a flowchart of the Test and Calibration Routine of FIG. 4.

After either the Initialization or the Restoration Routine has been executed, the Test and Calibration Routine of FIG. 7 is called. The Test and Calibration Routine first tests the EPROM and RAM of the main CPU 64 and sets an appropriate error flag in the event a failure is detected. Then the voltage of the battery 106 is measured and tested. In this embodiment, if the battery voltage is greater than 12.6 volts, the state of charge of the battery is considered acceptable. At this point, the relay 110 is controlled to charge the battery 106 for 10 minutes and the battery voltage after charging is monitored for an increase of approximately 0.2 volts. If this increased voltage is measured, the reaction of the battery to charging current is considered acceptable. Otherwise, an appropriate error flag is set. Then various other components of the home unit 60 are checked. For example, the A-D zero offset is measured and the zero reading for the scale module 84 and the ECG module 88 are measured and stored. The reading of the temperature module 86 is compared with a value indicative of normal room temperature and checked for reasonableness. Finally, the battery charger 108 is turned on with the relay 110 and the voltage of the battery is checked. If the battery charger 108 is operating properly, battery voltage should increase by about 1.3 volts during operation of the charger 108. In the event any failure is detected an appropriate error flag is set. Finally, the modem is tested with conventional methods, and an error flag is set in the event a failure is detected.

Returning to FIG. 4, after the Test and Calibration Routine of FIG. 7 has been executed, the various error flags are checked. In the event an error was detected the error is logged and the Exception Handler of FIG. 16 is called. Otherwise, the program advances to the Normal Operation Routine of FIG. 8.

Figure 8:
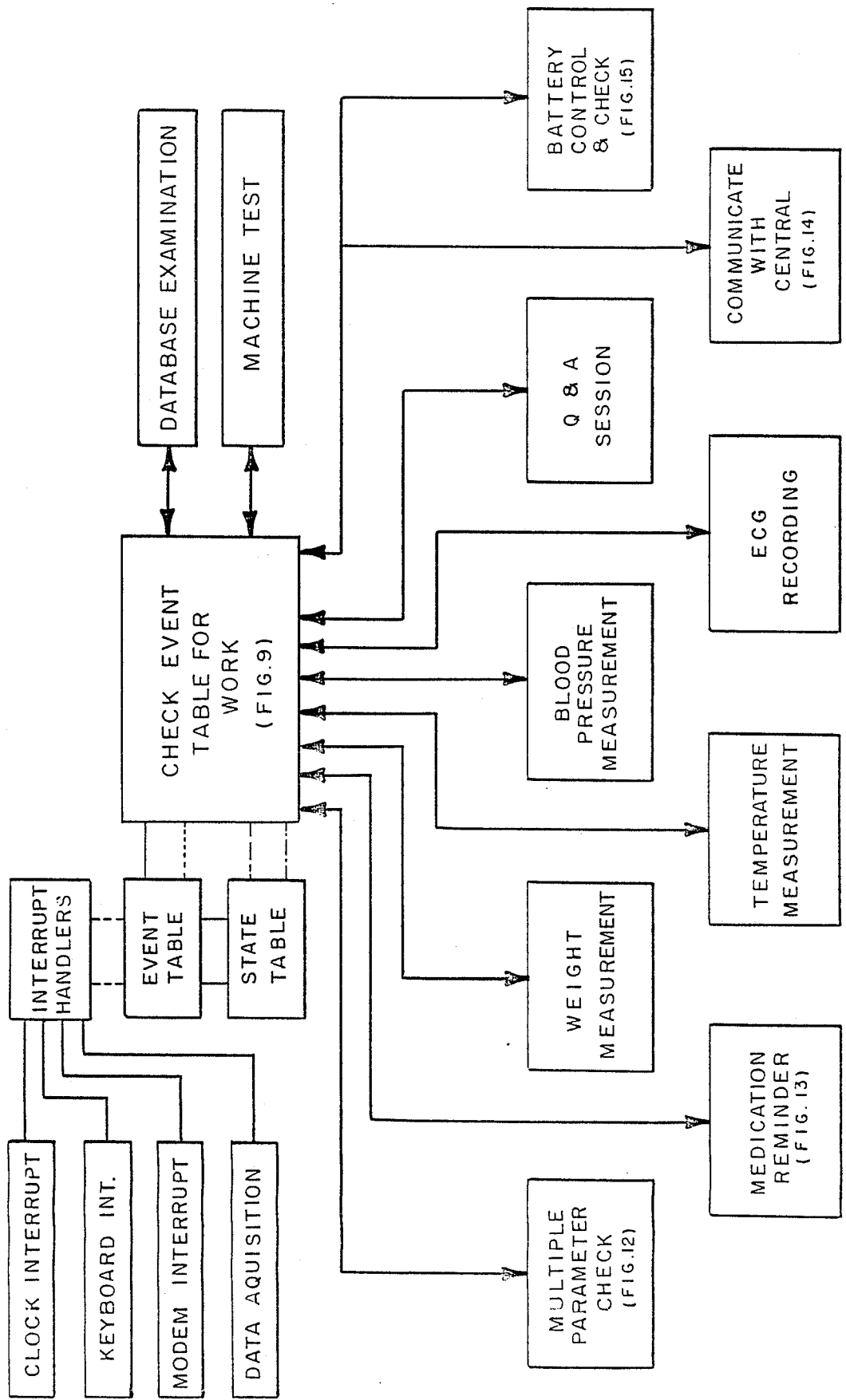
FIG. 8 is a block diagram showing the general organization of the Normal Operation Routine of the flowchart of FIG. 4.

FIG. 8 is a block diagram of the Normal Operation Routine referenced in the flowchart of FIG. 4. The Normal Operation Routine is a continuous loop which is flowcharted in FIG. 9. This loop is interrupted by various interrupts as shown in FIG. 8. The clock interrupt is used to maintain various real time clocks and timers in the program. The keyboard interrupt services user depressed keys, and the modem interrupt services the modem. The data acquisition interrupt services appropriate ones of the sensor modules.

As shown in FIG. 8, two tables, the event table and the state table, are maintained by the CPU 64. The event table includes test and medication schedules obtained from the test and medication profiles. In particular, the event table includes the following schedules: medication schedule, blood pressure test schedule, ECG test schedule, temperature test schedule, weight measurement schedule, and next central unit call schedule. Each of these schedules lists one or more times at which the respective tests will be performed. In addition, the event table stores the time of the last battery charge and the time of the predicted next required battery charge based on battery usage. Finally, the event table stores the time and identification of the next scheduled test.

The state table records such information as the communication state flag (which reflects the status of the modem), the battery-condition flag (which reflects the state of charge of the battery), and the multiple-test or single-test flag. As explained in greater detail below, this embodiment includes means for correlating multiple test parameters if requested by the physician. Such multiple parameter correlation is termed a multiple parameter check in the flowchart of FIG. 12. The state table also includes a variable which designates the current state of the system; i.e., whether the battery is being charged, communication is in process with the central unit, a test is being performed, or the like.

The blocks at the bottom of FIG. 8 indicate the various events that may be commanded by the CPU 64. The multiple parameter check event is flowcharted in FIG. 12, the medication reminder event is flowcharted in FIG. 13, the communication with central unit event is flowcharted in FIG. 14, and the battery control and check event is flowcharted in FIG. 15. The remaining events are measurements of parameters indicative of the health of the patient. In the weight measurement event, the patient is prompted to use the scale module 84, and a digital number indicative of the measured weight of the patient is stored in the composite log. Similarly, in the temperature measurement event, the patient is prompted to use the temperature module 86 to measure the patient's body temperature, and the measured body temperature is stored in the composite log. The blood pressure measurement event results in the CPU storing data indicative of measured pulse rate and systolic and diastolic blood pressure of the patient. The ECG recording event records in digital form the ECG waveform of the patient. At present, a sampling rate of between 200 and 300 Hertz is preferred, and the ECG waveform is digitized with a resolution of 12 bits. The digitized waveform is stored in the composite log for later transmission to the central unit in a time compressed form.

Finally, the question and answer session event is a series of questions which are presented to the patient via the display unit 68. Patient responses to these questions are recorded in the composite log. As explained in greater detail below, the particular questions asked of the patient are varied depending on both the physician prescribed schedule, and the measured health parameters.

Figure 9:
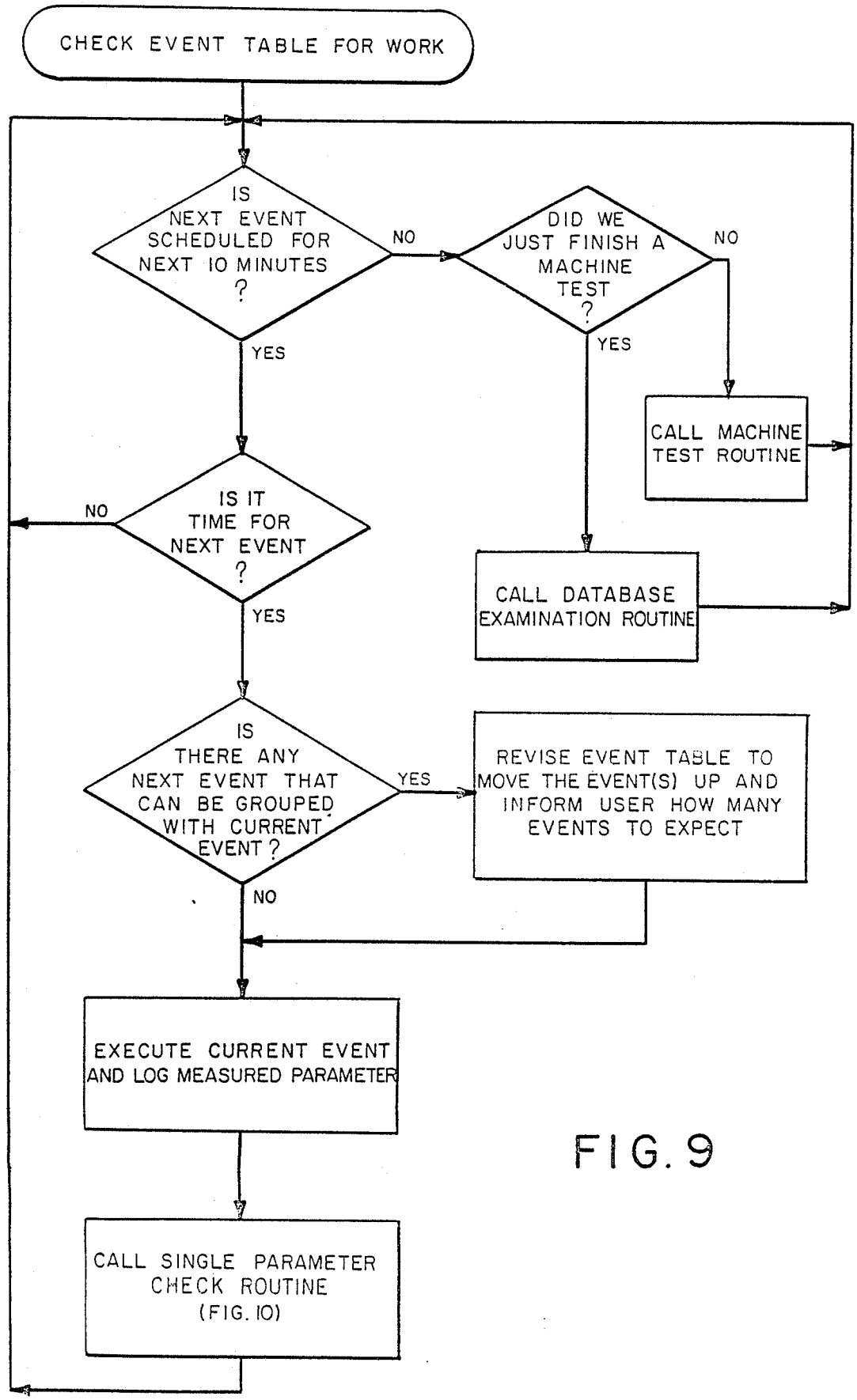
FIG. 9 is a flowchart of the Check Event Table for Work Routine of FIG. 8.

Turning to FIG. 9, the Check Event Table for Work Routine shown in block diagram form in FIG. 8 first checks to determine whether a next event is scheduled for the next ten minutes. If not, the routine performs either a Data Base Examination Routine or a Machine Test Routine. The Machine Test Routine performs standard diagnostic tests on the RAM, EPROM, and CPU of the home unit 60. The Data Base Examination Routine is not described in detail here, but it uses available processing time to analyze the patient information collected over time for trends and daily cycles. After either the Machine Test Routine or the Data Base Examination Routine has been completed, the program again checks to determine if the next event is scheduled to be performed within the next ten minutes. If so, the program continues to loop until it is time for the next event. The program then checks to see if multiple events can be grouped in order to minimize repeated interruptions to the patient. For example, if a non-critical medication event is scheduled to be performed ten minutes after a blood pressure measurement, the program of FIG. 9 will revise the event table to synchronize the two events and will inform the user of how many events to expect. Then the current event is executed and the measured data entered in the composite log, as described above. After the current event has been executed, the program executes the Single Parameter Check Routine of FIG. 10 and then again checks to determine if the next event is scheduled in the next ten minutes.

Figure 10:
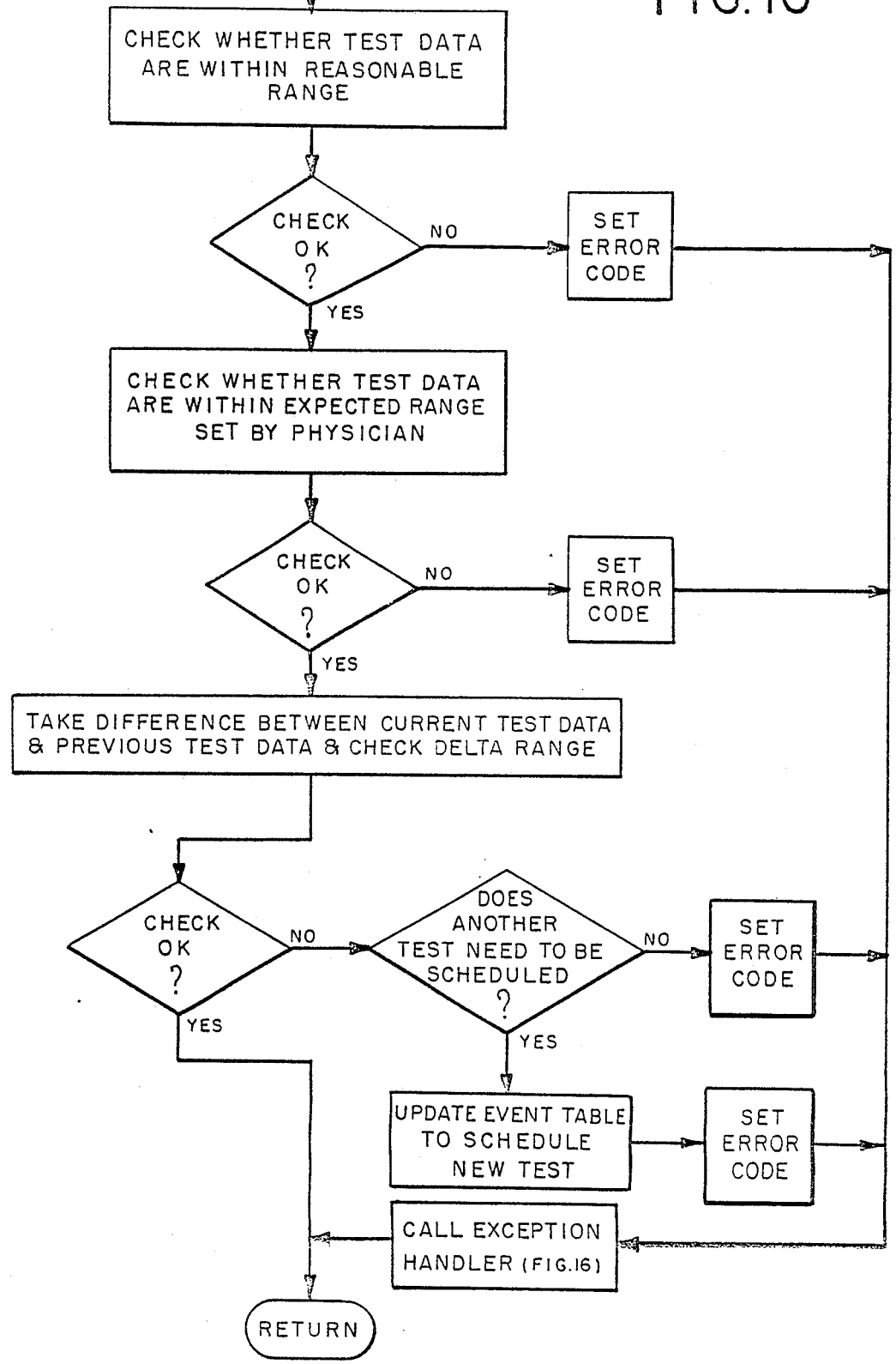
FIG. 10 is a flowchart of the Single Parameter Check Routine of FIG. 9.

The flowchart of FIG. 10 describes the Single Parameter Check Routine. First, the measured test data are checked for reasonableness. If the data are completely out of the range of reasonable results, indicating a sensing failure such as a sensor failure for example, an appropriate error code is set and the Exception Handler of FIG. 16 is called before the routine returns. Otherwise, the test data are checked to determine whether they are within the expected range set for this particular patient by the physician. If not, an appropriate error code is set and the Exception Handler of FIG. 16 is called before the routine returns. Otherwise, the routine takes the difference between the current test data and previous test data and checks the delta range. If the delta range is within expected limits, the routine returns. Otherwise, the routine determines whether another test should be scheduled to supplement the information stored in the composite log. If so, the event table is updated to schedule the new test and the routine returns. Otherwise, an appropriate error code is set and the exception handler of FIG. 16 is called before the routine returns.

Figure 11:
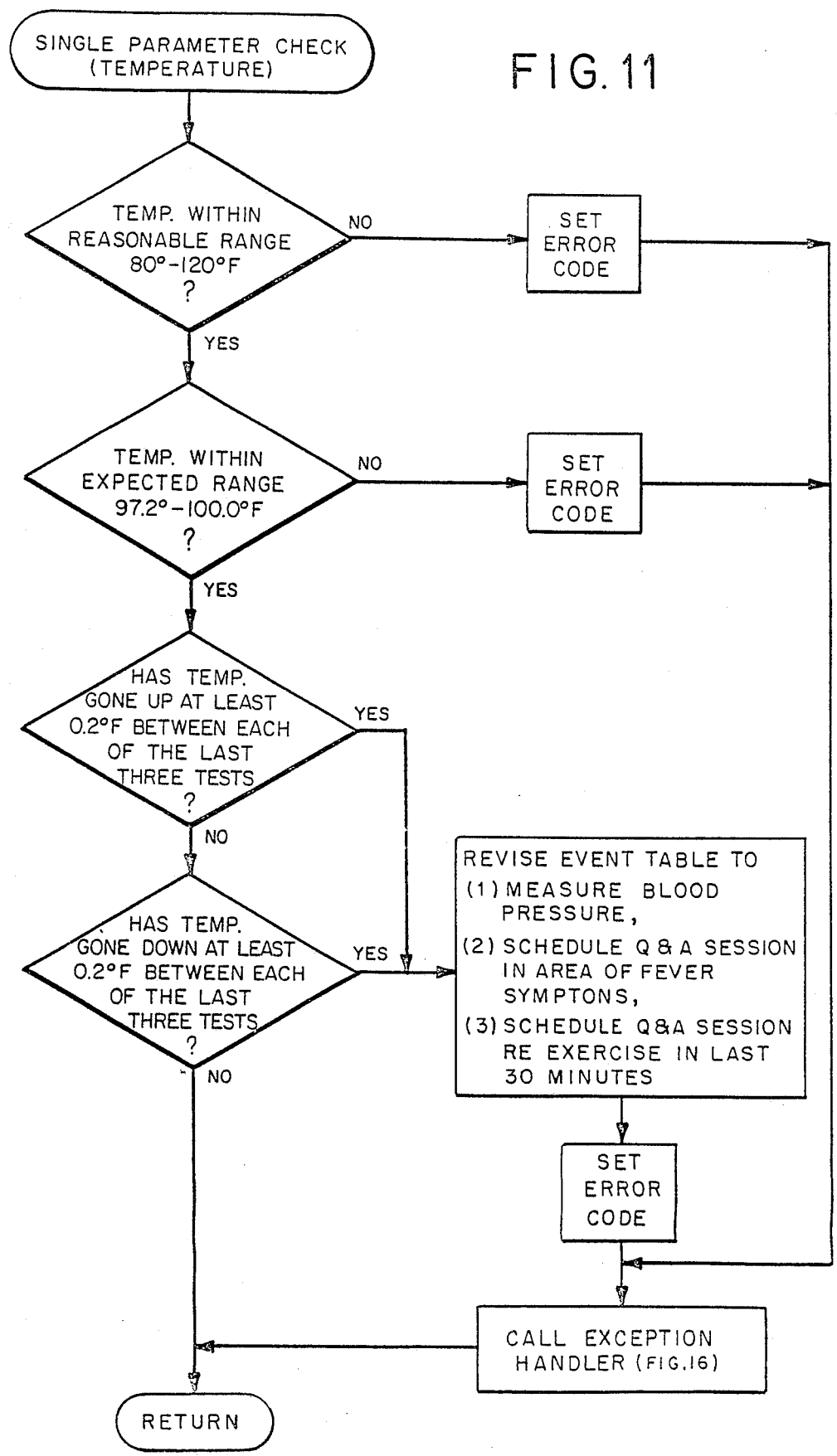
FIG. 11 is a specific example of one suitable Single Parameter Check Routine for patient temperature.

A separate Single Parameter Check Routine is provided for each parameter. FIG. 11 is an example of a Single Parameter Check Routine appropriate for use with the body temperature parameter. First, the routine of FIG. 11a checks to determine whether the temperature is within the reasonable range of 80°-120° F. If not, the routine assumes a sensing failure, sets an appropriate error code, calls the Exception Handler of FIG. 16, and returns. Otherwise, the routine checks to determine whether the measured temperature is within the physician specified expected range, 97.2°-100.0° F. in this example. The routine of FIG. 11 then checks the delta range by determining whether the temperature has gone up at least 0.2° F. for each of the last three tests, or has gone down at least 0.2° F. for each of the last three tests. Either condition is taken as indicative of a potentially significant trend, and the event table is revised to obtain additional diagnostic information that will be helpful to medical personnel at the central unit in interpreting the significance of the temperature trend. In this example, the event table is revised to measure blood pressure, to schedule a question and answer session in the area of fever symptoms, and to schedule a question and answer session regarding exercise patterns for the last thirty minutes. For example, the question and answer sessions could include the following:

Have you exercised in the last 30 minutes?
Do you feel you have a fever?
If so, is your fever continuous or intermittent?
Are you sweating?
Is your skin tender to the touch?

Then an appropriate error code is set and the Exception Handler of FIG. 16 is called.

Depending on the questions included in the question and answer session, patient answers to selected questions may also be used to select additional tests or questions to be used to supplement the log. For example, the question and answer session for a hypertensive patient who has been prescribed medication to control his blood pressure may include the question "Do you have a headache?" If the patient responds in the affirmative, and the composite log indicates that the prescribed medication has been taken, the Single Parameter Check Routine of this example will update the event table to schedule a blood pressure measurement. The blood pressure measurement will in many cases assist the physician at the central station in interpreting the significance of the patient's headache.

FIGS. 10 and 11 illustrate one important feature of this invention. The monitor collects a first set of test data (which in the example of FIG. 11 includes patient temperature), and then compares this first set of data with pre-selected test criteria. In the event the first set of data fail to correspond to the pre-selected test criteria, the monitor collects additional data (in the example of FIG. 11, data regarding blood pressure, fever symptoms and exercise patterns), all of which are stored in the composite log. These additional data assist trained medical personnel in interpreting the significance of the original data which failed to meet the test criteria. Thus, when the composite log is transmitted to the central unit, it provides information needed to diagnose the state of the patient which is more complete than if only the first set of data had been taken. Furthermore, this benefit is obtained without subjecting the patient to unnecessary tests. For example, in the routine of FIG. 11, the patient is not subjected to an unnecessarily large number of blood pressure tests or question and answer sessions related to fever symptoms or exercise patterns. These data are only collected in the event the need for the data is indicated by the measured patient temperature.

Figure 12:
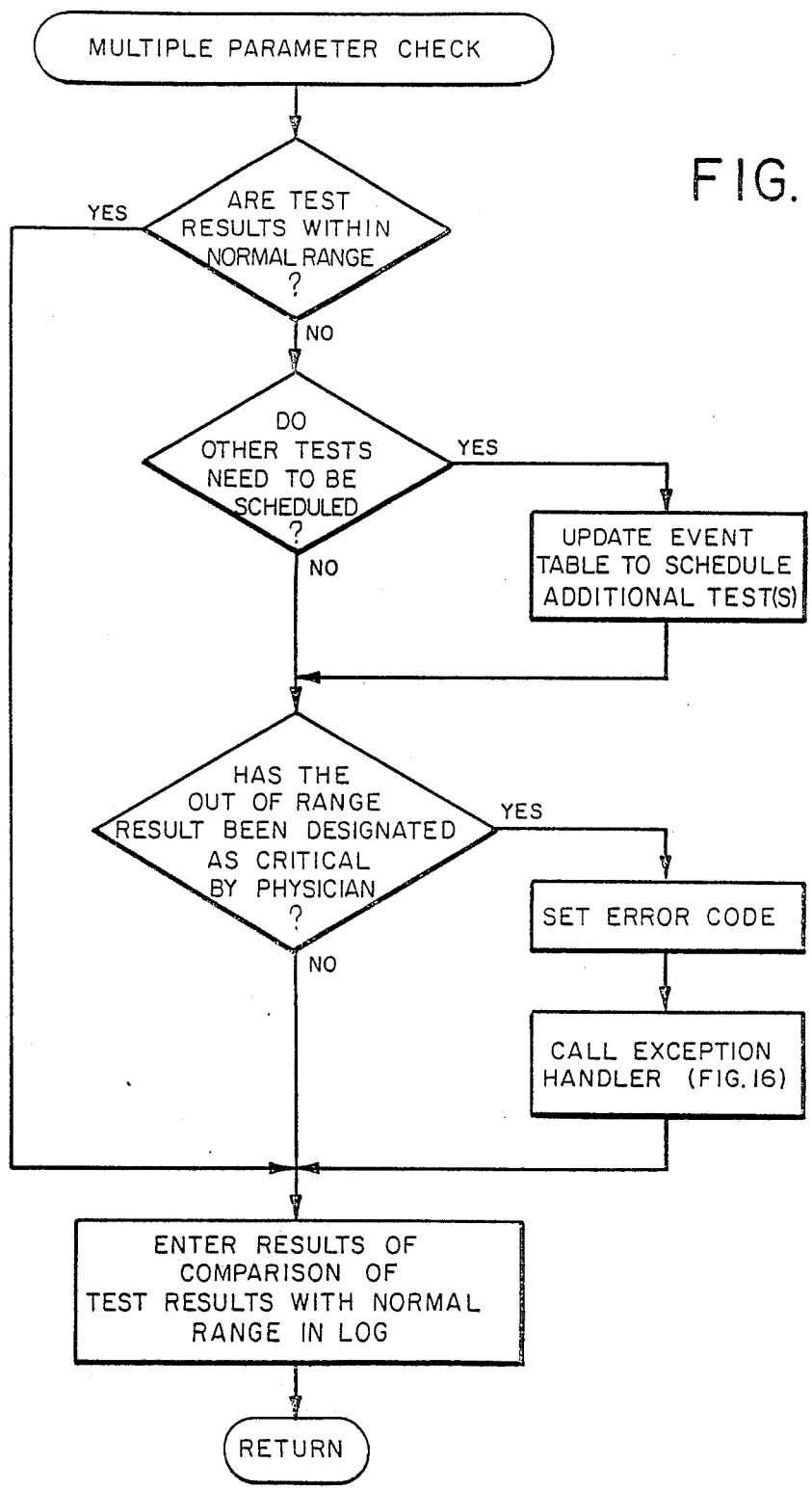
FIG. 12 is a flowchart of the Multiple Parameter Check Routine of FIG. 8.

FIG. 12 is a flowchart of the Multiple Parameter Check Routine. This routine first checks to determine whether the test results are within the normal range. If the test results are within the normal range as described below the routine enters the results of the comparison in the log and returns. Otherwise, the routine checks to determine whether additional tests are needed to supplement the log and if so updates the event table to schedule the additional tests. Then, the out-of-range result is checked to determine whether it has been designated as critical by the physician. If so, an error code is set to cause the Exception Handler to call the central unit ahead of schedule and the Exception Handler is called. If the physician has not designated the result as critical, the routine updates the log and returns.

As shown in Tables I and II, the multiple parameter check routine cross correlates multiple parameters in determining whether the test results are within the normal range. Thus, the normal range for a given parameter such as patient temperature, for example, varies in accordance with the measured value of another parameter, such as patient pulse rate or compliance with the medication schedule.

In Tables I and II, the rows and columns indicate respective parameters that are cross-correlated and the table entries indicate whether respective values of the parameters are considered normal (N) or abnormal (A).

TABLE I

Multiple Parameter Check for Pulse Rate and Body Temperature

| | Body Temperature | | |
|---|---|---|---|
| | Less than 98.7° F. | 98.7–100.0° F. | Greater than 100° F. |
| Pulse Rate less than 65 Beats per minute (BPM) | N | N | A |
| Pulse Rate 65–99 BPM | N | N | A |
| Pulse Rate greater than 99 BPM | A | N | N |

Table I is based on that fact that for many patients, an inverse correlation between pulse rate and body temperature is diagnostically significant. That is, the combination of an elevated temperature combined with a depressed pulse rate is more likely to indicate a developing health problem than is the combination of elevated temperature and elevated pulse rate.

TABLE II

Multiple Parameter Check for Blood Pressure Measurements and Medication Compliance

| | Blood Presure (mm Hg) | | | |
|---|---|---|---|---|
| | Systolic greater than 140 | Diastolic greater than 90 | Systolic 140 or less | Diastolic 90 or less |
| Medication taken as prescribed | A | A | N | N |
| Medication not taken as prescribed | N | N | N | N |

In the example of Table II, it is assumed that the patient has been prescribed medication to control blood pressure, and that a sufficient time to allow the medication to become effective has elapsed between the patient response indicating whether the medication was taken and the blood pressure measurement. Of course, the particular systolic and diastolic pressures used in Table II will be set by the physician as appropriate for the particular patient. Regardless of the particular pressures chosen, the example of Table II classifies as abnormal only the combination of elevated blood pressure and patient compliance with the prescribed medication schedule. Of course, the Single Parameter Check Routine for blood pressure measurement and medication compliance will already have checked these parameters as described above to determine whether they are within the expected ranges set by the physician.

In other applications the parameters which are cross-correlated and the values used to define normal and abnormal situations will all be set as prescribed for the particular patient by the particular attending physician. In some situations three or more parameters may be cross-correlated. The cross-correlation of multiple parameters may be accomplished with a wide variety of computational and storage techniques, including the matrix approach of Tables I and II and the use of polynomial equations employing health parameters of the patient as variables.

FIG. 12 and Tables I and II illustrate another important feature of this invention. The preferred embodiment of the monitor of this invention cross-correlates multiple parameters in order to alert the central unit in the event of a potentially dangerous situation, while minimizing the number of false alarms. Because the normal range for a single parameter is made to vary in accordance with the measured value of one or more other parameters, the monitor can better distinguish between potentially dangerous situations, in which the central unit should be notified promptly, and routine deviations of measured health parameters.

Figure 13:
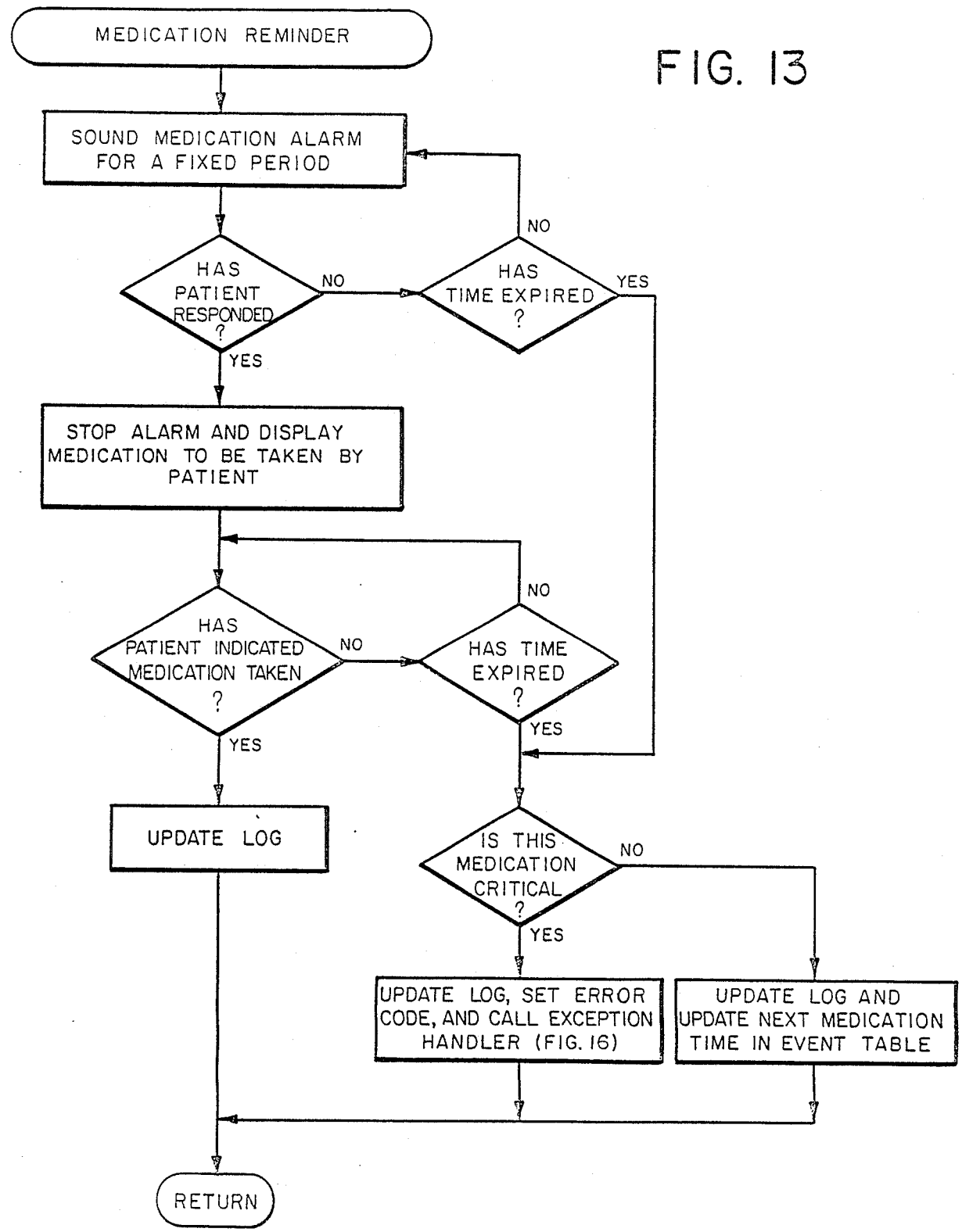
FIG. 13 is a flowchart of the Medication Reminder Routine of FIG. 8.

FIG. 13 shows a flowchart of the Medication Reminder Routine. Once the event table has indicated that a medication event is to be performed and the Medication Reminder Routine has been called, a medication alarm is sounded for a fixed period. Once the patient responds to the alarm, the routine stops the alarm and displays a message which indicates to the patient the medication to be taken and requests the user to use the key pad 74 to indicate that the displayed medication has been taken. Once the medication has been taken, the composite log is updated to record the medication event and the routine returns. In the event the patient fails to respond to the initial alarm for a predetermined time period, or in the event the patient fails to indicate that the displayed medication has been taken within a predetermined time period, the routine checks to determine whether the particular medication has been designated as critical by the physician. If so, the routine updates the log to indicate a failure of the patient to take the scheduled medication, sets an error code that will result in a prompt communication with the central unit, and calls the Exception Handler of FIG. 16. Otherwise, the failure of the patient to take the scheduled medication is recorded in the composite log, and the next medication time in the event table is updated before the routine returns.

The routine of FIG. 13 illustrates yet another important feature of this invention. The composite log includes both information indicative of measured health parameters of the patient and information indicative of the schedule with which prescribed medication was actually taken by the patient. By providing trained personnel at the central unit with both types of information, the diagnostic value of the composite log is materially enhanced. Furthermore, the routine of FIG. 13 automatically notifies the central unit promptly after a critical medication event has been missed.

Figure 14:
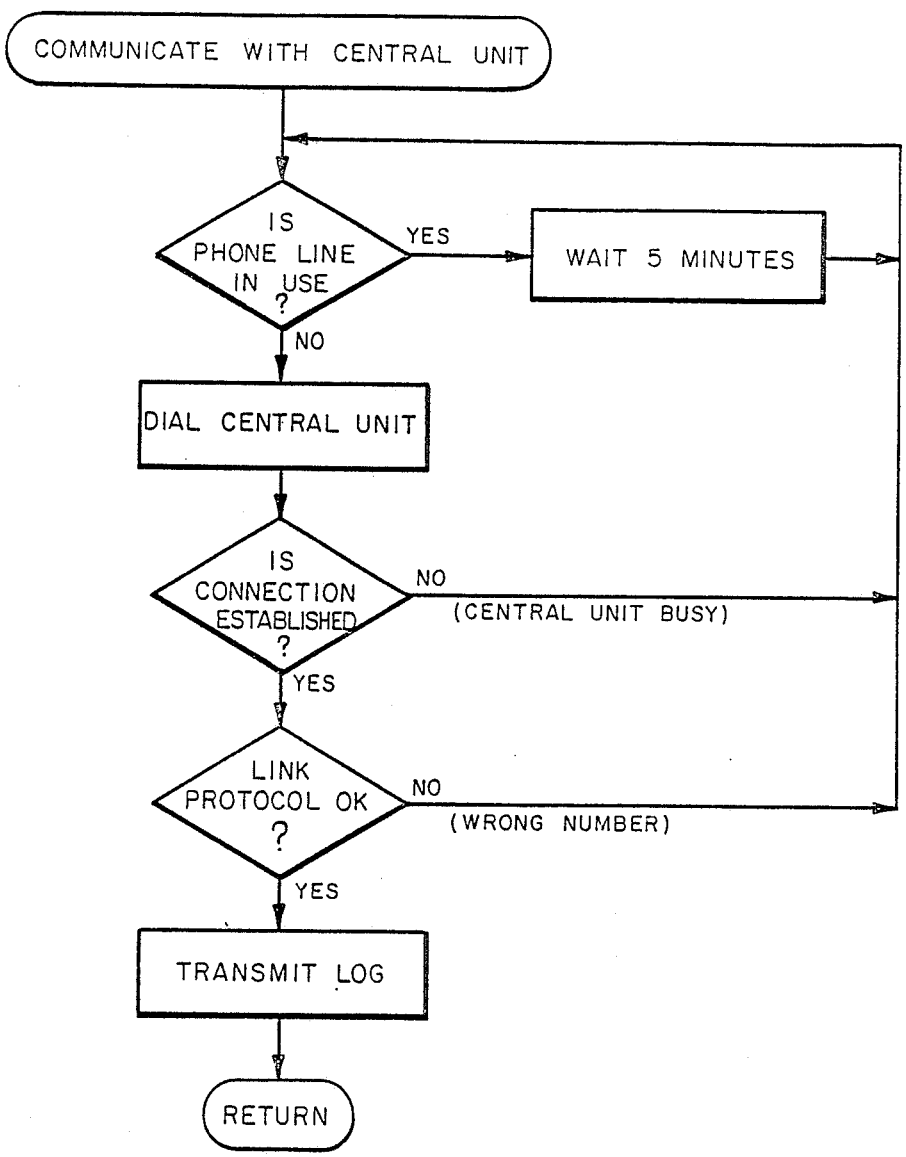
FIG. 14 is a flowchart of the Communicate With Central Unit Routine of FIG. 8.

FIG. 14 provides a flowchart of the Communication With Central Unit Routine. This routine first checks to determine if the phone line is in use. If so, the routine waits five minutes and then tries again. Once the phone line is free, the routine dials the central unit and checks to see whether a connection has been established. If no connection was established, the routine tries again. Once a connection has been established, the routine checks to determine whether the proper link protocol has been received. If not, the routine assumes a wrong number was obtained and tries again. Once the link protocol has been received, the routine transmits the log via the modem 22 and then returns.

Figure 15:
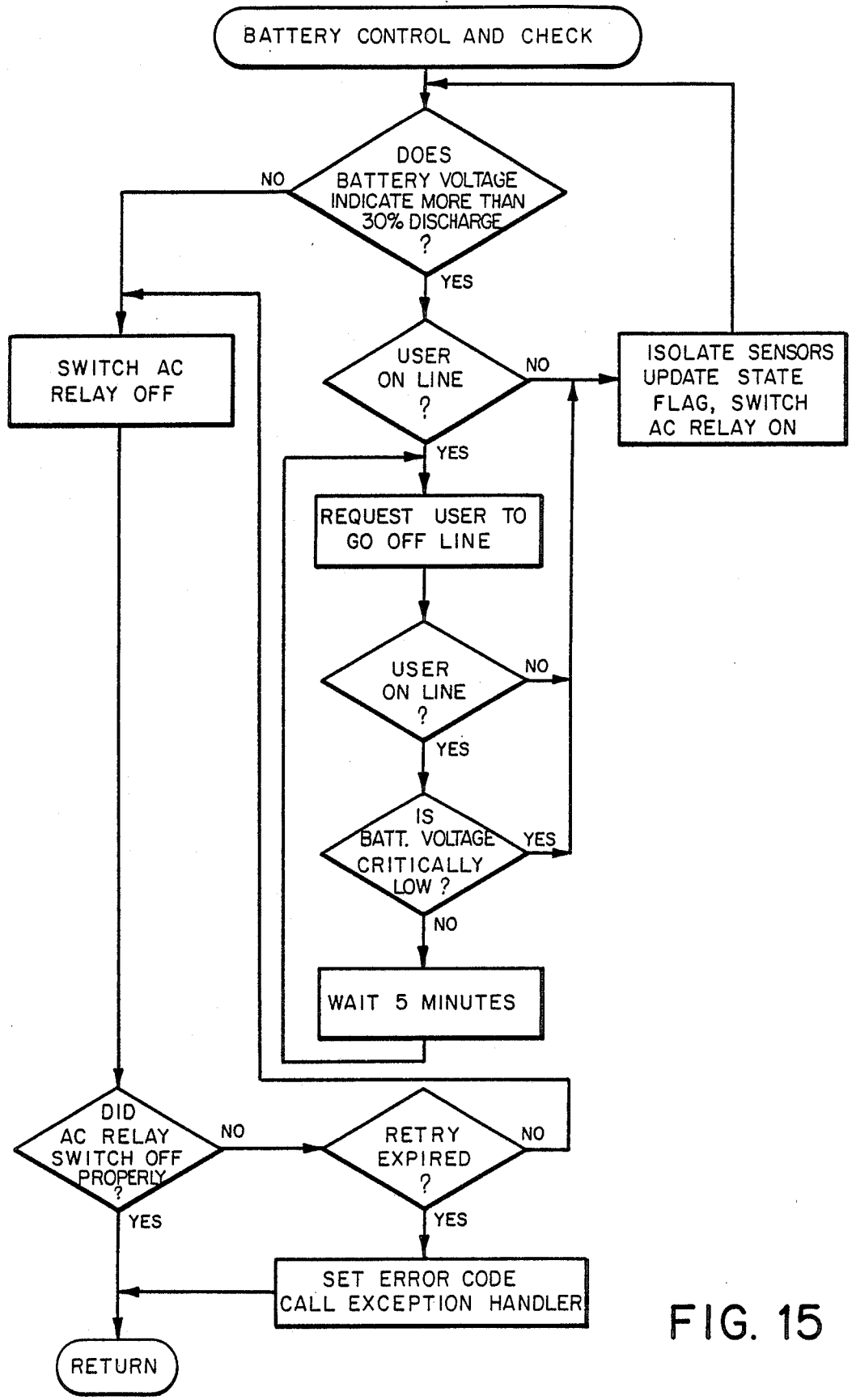
FIG. 15 is a flowchart of the Battery Control and Check Routine of FIG. 8.

FIG. 15 is a flowchart of the Battery Control and Check Routine. This routine is executed once every four hours as well as whenever the keyboard interrupt responds to user depression of a key of the key pad 74 or the keyboard 76. In addition, the routine of FIG. 15 is executed whenever a medication event or a test event (including a question and answer session) is executed. The routine first checks to determine whether the battery voltage is sufficiently low to indicate that the battery is more than 30% discharged. If so, the routine checks to determine whether a user is on-line, and, if necessary, requests the user to go off line for thirty minutes while the battery is charged. If the user remains on line, the routine then checks to determine whether the battery voltage is critically low. If so, the routine isolates the ECG sensors with the relay 91, updates the state flag, and controls the AC relay 110 to switch the relay to the on state, thereby connecting the battery charger 108 to the AC power source. In the event the battery voltage is not critically low, the routine waits five minutes and again requests the user to go off line. In the event the battery voltage indicates a discharge level of less than 30%, the routine switches the AC relay 110 to the off state and then checks to insure that the relay 110 has responded properly. If so, the routine returns. Otherwise, the routine again attempts to switch the AC relay 110 to the off state. Repeated failures of the AC relay 110 to respond cause the routine to set an appropriate error code to and call the Exception Handler of FIG. 16 before returning.

FIG. 15 illustrates another important feature of this invention. By controlling the relay 110 to disconnect the battery charger 108 from the AC power source, the routine of FIG. 15 insures that AC ripple voltages are absent from the regulated DC voltages during selected periods. This simplifies and minimizes the expense of certain measuring hardware. For example, the ECG module 88 can be much simplified because of the absence of AC ripple voltages during an ECG test event. In that the AC ripple voltages are not present, the ECG module 88 does not need sophisticated electronic circuitry to stabilize input voltages. Furthermore, when the ECG waveform is being recorded, it is important that the ECG electrodes present no danger to the patient. The routine of FIG. 15 insures that the battery charger is disconnected from the AC power source during an ECG test, and thereby eliminates the need for opto-isolators or the like to protect the patient from undesired and potentially dangerous contact with the AC power source.

FIG. 16 provides a flowchart of the Exception Handler. This routine first checks the error code to determine whether the current error is a hardware error. If so, and the error is recoverable, the routine re-initializes, recovers from the error, logs the error, and returns. Otherwise, the routine checks to determine whether the modem is functioning and whether a call can be completed to the central unit. If so, the routine updates the event table to report the error to the central unit and returns. Otherwise, the routine alerts the user to telephone the central unit manually and report the error.

In the event the error code indicates a procedure error, the routine recovers from the error, displays and logs the error, and returns In the event the error code indicates a range error such that the measured data are outside of the reasonable range (indicating a probable hardware problem), the routine sets a retry flag in order to repeat the out-of-range measurement. Otherwise, the routine logs the error and revises the event table to call the central unit. In the event the data are within the reasonable range, the routine checks to determine whether the parameter has been selected as critical by the physician. If so, the error is logged and the event table is revised to call the central station and to transmit the patient log. Otherwise, the error is logged and the routine returns.

From the foregoing, it should be apparent that an improved personal health monitor has been described which includes various features that enhance its efficiency and usefulness. By including both information relating to medication events and test events in the composite log, the diagnostic value of the composite log is markedly increased. By automatically disconnecting the battery charger from the AC power source at certain times, the cost and complexity of components such as the ECG module are reduced. By varying the normal range of values for a given parameter based on the measured values of other parameters, the central unit is notified of potentially dangerous situations while minimizing false alarms. By collecting additional data only when a first set of data falls outside the range of expected values, the diagnostic value of the composite log is increased without unnecessary inconvenience to the patient. All of these advantages are provided with a personal health monitor that can be constructed from proven, conventional hardware.

Of course, it should be understood that a wide range of changes and modifications can be made to the preferred embodiment described above. For example, specific hardware components can readily be modified or adapted as needed to suit individual applications. The particular array of sensor modules included in any given health monitor can easily be modified to suit the particular application. Furthermore, if desired, the central unit can be interconnected with the home units by radio links or by hardwire links rather than via the modems described above. Of course, the specific test and medication profiles and the specific questions included in the question and answer sessions will be modified for each application as requested by the attending physician. In addition, the techniques used to select additional tests to be performed or questions to be asked, and the techniques used to modify the normal range for first parameter based on a second parameter can be varied widely. As pointed out above, each of the improvements of this invention can be used alone or in combination with any of the other improvements.

It is therefore intended that the foregoing detailed description be regarded as illustrative rather than limiting, and that it be understood that it is the following claims, including all equivalents, which are intended to define the scope of this invention.

We claim:

1. A personal health monitor comprising:

means for determining a plurality of health parameters, each indicative of the physical condition of a patient;

means for prompting the patient with selected messages;

means for storing a prescribed parameter schedule for selected ones of the health parameters;

means for storing a prescribed medication schedule for at least one medication;

first means for automatically controlling the prompting means to request the patient to use the determining means to determine selected ones of the health parameters in accordance with the prescribed parameter schedule and for automatically storing the determined health parameters in a composite log;

second means for automatically controlling the prompting means to request the patient to take medication in accordance with the prescribed medication schedule;

means for automatically recording in the composite log information indicative of patient compliance with the prescribed medication schedule; and means for automatically transmitting the composite log to a central location for analysis by trained medical personnel;

said composite log providing information indicative of both the determined health parameters and patient compliance with the prescribed medication schedule at the central location, thereby assisting the trained medical personnel in assessing the health of the patient.

2. The invention of claim 1 wherein the plurality of health parameters comprises: patient weight, patient temperature, patient pulse rate, patient blood pressure, and patient responses to selected questions.

3. The invention of claim 1 wherein the prescribed medication schedule comprises a plurality of medication events, and wherein the information recording means records information in the composite log indicative of a plurality of medication times, each corresponding to the time a respective one of the medication events was performed by the patient.

4. The invention of claim 3 wherein the prescribed parameter schedule comprises a plurality of test events, and wherein the first means additionally stores in the composite log information indicative of a plurality of test times, each corresponding to the time a respective one of the health parameters was determined.

5. The invention of claim 1 wherein the transmitting means comprises a modem.

6. The invention of claim 1 wherein the personal health monitor further comprises means for automatically controlling the transmitting means to transmit the composite log to the central location on a schedule composite log.

7. A personal health monitor adapted to be powered by an alternating circuit power source, said monitor comprising:

means for collecting information indicative of the physical condition of a patient;

means for recording the collected information; and means for supplying a DC supply voltage to power the collecting means and the recording means, said supplying means comprising:

a rechargeable battery connected to the collecting means and the recording means;

a battery charger adapted for connection to the alternating circuit power source and comprising means for supplying a charging current to the battery;

a switch positioned to interrupt the flow of charging current from the battery charger to the battery and switchable between a first state, in which the switch isolates the battery from the charging circuit, and a second state, in which the switch allows the charging current to flow to the battery;

first means for automatically placing the switch in the first state during at least selected periods of interaction between the patient and the collecting means; and second means for automatically placing the switch in the second state during at least selected periods characterized by an absence of interaction between the patient and the collecting means.

8. The invention of claim 7 wherein the switch comprises a relay.

9. The invention of claim 7 wherein the collecting means comprises a plurality of patient sensors, each comprising means for sensing a respective patient parameter, and wherein the first means places the switch in the first state whenever selected ones of the patient sensors are operating to sense the respective patient parameter.

10. The invention of claim 7 wherein the collecting means comprises a patient input device, and wherein the first means places the switch in the first state during at least selected periods when the patient input device is in use.

11. The invention of claim 7 wherein the rechargeable battery comprises a lead acid battery.

12. A personal health monitor adapted to be powered by an alternating current power source, said monitor comprising:

a patient monitor comprising at least a display, a blood pressure sensor, a patient temperature sensor, a patient weight sensor, a controller which comprises means for presenting messages to a patient via the display, means for recording readings from the sensors in a log, and means for transmitting the log to a central location for analysis by trained medical personnel;

a rechargeable battery;

means for supplying power from the battery to the patient monitor;

a battery charger adapted for connection to the alternating current power source and comprising means for supplying a charging current to the battery;

a switch interposed between the battery and the alternating current power source and switchable between a first state, in which the switch isolates the battery from the alternating current power source, and a second state, in which the switch interconnects the battery and the alternating current power source via the battery charger;

first means, includes in the patient monitor, for automatically placing the switch in the first state whenever the means for recording readings from the sensors is operative in order to insure that the alternating current power source patients to danger to the patient and no disturbing influence to the readings from the sensors; and second means for automatically placing the switch in the second state during at least selected periods characterized by an absence of interaction between the patient and patient monitor.

13. The invention of claim 12 wherein the switch comprises a relay.

14. The invention of claim 12 wherein the patient monitor further comprises a keyboard, and wherein the patient monitor further comprises means for automatically placing the switch in the first state during at least selected periods when the keyboard is in use.

15. The invention of claim 12 wherein the rechargeable battery comprises a lead acid battery.

16. A personal health monitor comprising:

first means for automatically collecting a first set of data indicative of a first set of parameters indicative of the physical condition of a patient;

second means for automatically comparing the first set of data with a set of test criteria and for indicating when the first set of data fails to meet the test criteria;

third means for automatically collecting a second set of additional data from the patient only when the first set of data fails to meet the test criteria, said second set of additional data indicative of at least one additional parameter, not included in the first set of parameters, selected to provide additional diagnostic information useful in interpreting the first set of data; and fourth means for automatically transmitting the first and second sets of data to a central location for analysis by trained medical personnel;

wherein the first set of data comprises information indicative of at least one physical measurement of a parameter included in the first set of parameters and indicative of the physical condition of the patient;

wherein the second set of data comprises information indicative of at least one physical measurement of said additional parameter.

17. The invention of claim 16 wherein the first set of data also comprises information indicative of at least one answer supplied by the patient to a question presented by the first means related to a parameter included in the first set of parameters.

18. The invention of claim 16 wherein the second set of data also comprises information indicative of at least one answer supplied by the patient to a question presented by the third means related to a parameter included in the second set of parameters.

19. A personal health monitor comprising:
a patient monitor adapted for home use, comprising at least a display, a patient answer input device, a plurality of sensors including blood pressure sensor, a patient temperature sensor, and a patient weight sensor, and a controller which comprises first means for presenting messages including questions to a patient via the display, second means for recording patient answers to selected ones of the questions and readings from selected ones of the sensors in a log, and third means for automatically transmitting the log to a central location for analysis by trained medical personnel;
means, included in the second means, for automatically collecting a first set of data from a first selected set of sensors and questions and recording said first set of data in the log;
means for automatically comparing the first set of data with a set of test criteria and for indicating when the first set of data deviates excessively from the test criteria;
means, included in the second means and operative only when the first set of data deviates excessively from the test criteria, for automatically collecting a second set of additional data from a second selected set of sensors and questions and recording said second set of data in the log prior to transmission of the log by the third means, said second selected set of sensors and questions including at least one sensor or question not included in the first selected set of sensors and questions;
said second set of additional data selected to provide additional diagnostic information useful in interpreting the first set of data.

20. A person health monitor comprising:
means for automatically monitoring a plurality of parameters indicative of the physical condition of a patient, said plurality of parameters including at least first and second parameters selected such that the correlation between the first and second parameters is diagnostically significant;
means for storing information indicative of a selected range of normal values of the first parameter, said selected range of normal values varying in accordance with the second parameter such that the selected range of normal values when the second parameter has a first value is different from the selected range of normal values when the second parameter has a second value;
means for alerting a central station only when the first parameter is outside the selected range of normal values.

21. The invention of claim 20 wherein the alerting means comprises means for automatically transmitting the plurality of parameters to the central station for analysis by medical personnel.

22. A personal health monitor adapted for home use comprising:
a display;
a plurality of patient sensors including at least a blood pressure sensor, a patient temperature sensor, and a patient weight sensor;
a controller comprising first means for presenting messages of a patient via the display, second means for recording a plurality of patient parameters indicative of readings from selected ones of the sensors in a log; and third means for automatically transmitting the log to a central location for analysis by trained medical personnel;
means for storing information indicative of a selected range of normal values for a first one of the parameters, said selected range of normal values varying in accordance with a second one of the parameters such that the selected range of normal values when the second parameter has a first value differs from the selected range of normal values when the second parameter has a second value, said first and second parameters selected such that the correlation between the first and second parameters is diagnostically significant;
means for alerting the central location only when the first parameter is outside the selected range of normal values.

23. The invention of claim 22 wherein the alerting means controls the third means to cause immediate transmission of the log to the central station.

24. The invention of claim 22 wherein the patient sensors further include a patient answer input device, wherein the messages include questions, and wherein selected ones of the parameters are indicative of patient answers to selected questions.

25. A personal health monitor comprising:
first means for automatically collecting a first set of data indicative of a first set of parameters indicative of the physical condition of a patient;
second means for automatically comparing the first set of data with a set of test criteria and for indicating when the first set of data fails to meet the test criteria;
third means for automatically collecting a second set of additional data from the patient only when the first set of data fails to meet the test criteria, said second set of additional data indicative of at least one additional parameter, not included in the first set of parameters, selected to provide additional diagnostic information useful in interpreting the first set of data; and fourth means for automatically transmitting the first and second sets of data to a central location for analysis by trained medical personnel;

wherein the second set of data comprises information indicative of at least one physical measurement of said additional parameter.

26. The invention of claim 25 wherein the first set of data comprises information indicative of at least one physical measurement of a parameter included in the first set of parameters and indicative of the physical condition of the patient.

27. The invention of claim 25 wherein the first set of data comprises information indicative of at least one answer supplied by the patient to a question presented by the first means related to a parameter included in the first set of parameters.

28. The invention of claim 25 wherein the second set of data also comprises information indicative of at least one answer supplied by the patient to a question presented by the second means related to a parameter included in the second set of parameters.

29. A personal health monitor comprising:

means for automatically monitoring a plurality of parameters indicative of the physical condition of a patient, said plurality of parameters including at least first and second parameters selected such that the correlation between the first and second parameters is diagnostically significant;

means for storing information indicative of a selected range of normal values of the first parameter, said selected range of normal values varying in accordance with the second parameter such that the selected range of normal values when the second parameter has a first value is different from the selected range of normal values when the second parameter has a second value;

means for obtaining additional information regarding selected ones of the parameters only when the first parameter is outside the selected range of normal values.

30. A personal health monitor adapted for home use comprising:

a display;

a plurality of patient sensors including at least a blood pressure sensor, a patient temperature sensor, and a patient weight sensor;

a controller comprising first means for presenting messages to a patient via the display, second means for recording a plurality of patient parameters indicative of readings from selected ones of the sensors in a log; and third means for automatically transmitting the log to a central location for analysis by trained medical personnel;

means for storing information indicative of a selected range of normal values for a first one of the parameters, said selected range of normal values varying in accordance with a second one of the parameters such that the selected range of normal values when the second parameter has a first value differs from the selected range of normal values when the second parameter has a second value, said first and second parameters selected such that the correlation between the first and second parameters is diagnostically significant;

means, including in the controller, for recording in the log a plurality of patient parameters indicative of readings from selected additional ones of the sensors, only when the first parameter is outside the selected range of normal values.

* * * * *

UNITED STATES PATENT AND TRADEMARK OFFICE
CERTIFICATE OF CORRECTION

PATENT NO. : 4,803,625
DATED : February 7, 1989
INVENTOR(S) : Ping W. Fu et al.

Page 1 of 2

It is certified that error appears in the above-identified patent and that said Letters Patent is hereby corrected as shown below:

In column 3, line 68, after "desired." please insert the following sentence --The invention itself, together with further objects and attendant advantages, will best be understood by reference to the following detailed description, taken in conjunction with the accompanying drawings.--

In column 4, line 38, please delete "15a" and substitute therefor --16a--.

In column 17, between lines 41 and 42, after "schedule" please insert --determined at least in part by information included in the--.

In column 18, line 43, please delete "includes" and substitute therefor --included--.

In column 18, line 47, please delete "patients to" and substitute therefor --presents no--.

UNITED STATES PATENT AND TRADEMARK OFFICE
CERTIFICATE OF CORRECTION

PATENT NO. : 4,803,625

DATED : February 7, 1989

INVENTOR(S) : Ping W. Fu et al.

It is certified that error appears in the above-identified patent and that said Letters Patent is hereby corrected as shown below:

In column 20, line 27, please delete "of" and substitute therefor --to--.

In column 22, line 31, please delete "including" and substitute therefor --included--.

Signed and Sealed this

Twenty-eighth Day of April, 1992

Attest:

HARRY F. MANBECK, JR.

Attesting Officer     Commissioner of Patents and Trademarks